(12) United States Patent
Kim et al.

(10) Patent No.: US 12,184,796 B2
(45) Date of Patent: Dec. 31, 2024

(54) EDIBLE UNCLONABLE FUNCTIONS

(71) Applicant: Purdue Research Foundation, West Lafayette, IN (US)

(72) Inventors: Young L Kim, West Lafayette, IN (US); Jung Woo Leem, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/768,289

(22) PCT Filed: Aug. 15, 2020

(86) PCT No.: PCT/US2020/046580
§ 371 (c)(1),
(2) Date: Apr. 12, 2022

(87) PCT Pub. No.: WO2021/076217
PCT Pub. Date: Apr. 22, 2021

(65) Prior Publication Data
US 2024/0146547 A1    May 2, 2024

Related U.S. Application Data

(60) Provisional application No. 62/915,667, filed on Oct. 16, 2019, provisional application No. 62/915,666, filed on Oct. 16, 2019.

(51) Int. Cl.
*H04L 9/00* (2022.01)
*A61K 47/42* (2017.01)
(Continued)

(52) U.S. Cl.
CPC ............ *H04L 9/3278* (2013.01); *A61K 47/42* (2013.01); *G06Q 30/018* (2013.01)

(58) Field of Classification Search
CPC ....... H04L 9/3278; A61K 47/42; G06Q 30/18
See application file for complete search history.

(56) References Cited

U.S. PATENT DOCUMENTS 8,516,269 B1   8/2013   Hamlet et al.
8,750,502 B2 *  6/2014   Kirkpatrick ........... H04L 9/0866
                                                    714/E11.042
(Continued)

FOREIGN PATENT DOCUMENTS

CN    105130660 A    9/2015
EP    3340213 A1    6/2018
(Continued)

OTHER PUBLICATIONS

Kim et al., Revisiting silk: a lens-free optical physical unclonable function. Nature Communications 13, 247 (2022).
(Continued)

*Primary Examiner* — Khai M Nguyen
(74) *Attorney, Agent, or Firm* — Piroozi-IP, LLC

(57) ABSTRACT

A method of generating a physically unclonable function (PUF) for pharmaceutical authentication is disclosed which includes generating an edible (PUF), affixing the edible PUF onto a pharmaceutical in a random distribution, and generating a cryptographic key based on the randomly distributed and affixed edible PUF. The present disclosure generally relates to counterfeit measures, and in particular, to an arrangement concerning an edible unclonable function counterfeit measure.

24 Claims, 19 Drawing Sheets
Specification includes a Sequence Listing.

(51) Int. Cl.
G06Q 30/018 (2023.01)
H04L 9/32 (2006.01)

(56) References Cited

U.S. PATENT DOCUMENTS

| | | | |
|---|---|---|---|
| 11,323,275 B2* | 5/2022 | Mondello | H04L 63/0442 |
| 11,528,151 B2* | 12/2022 | Lu | H03K 19/0963 |
| 2002/0137211 A1 | 9/2002 | Liu et al. | |
| 2007/0048365 A1* | 3/2007 | Rao | A61K 9/2072 |
| | | | 424/464 |
| 2016/0320400 A1 | 11/2016 | Khan et al. | |
| 2017/0173262 A1* | 6/2017 | Veltz | G16H 20/17 |
| 2019/0213371 A1* | 7/2019 | Endress | G09C 1/00 |
| 2019/0334730 A1* | 10/2019 | Endress | H04L 9/3278 |
| 2020/0082235 A1 | 3/2020 | Gupta et al. | |

FOREIGN PATENT DOCUMENTS

| | | |
|---|---|---|
| WO | WO2009155397 A2 | 12/2009 |
| WO | WO2010044101 A1 | 4/2010 |

OTHER PUBLICATIONS

Li et al., Construction of transgenic silkworm spinning antibacterial silk with fluorescence. Molecular Biology Reports 42, 19-25 (2015).
Jaramillo-Quiceno et al., Water-annealing treatment for edible silk fibroin coatings from fibrous waste. Journal of Applied Polymer Science 137, 48505 (2020).
U.S. Food and Drug Administration, Summary of Color Additives for Use in the United States in Foods, Drugs, Cosmetics, and Medical Devices, May 2015.
Corradini et al., Identifying and selecting edible luminescent probes as sensors of food quality, AIMS Biophysics 3, 319-339 (2016).
Day et al., The fluorescent protein palette: tools for cellular imaging. Chemical Society Reviews 38, 2887 (2009).
Ghalei et al., Silk Nanoparticles: A Natural Polymeric Platform for Nitric Oxide Delivery in Biomedical Applications. ACS Appl. Mater. Interfaces, 12, 53615-53623, 2020.
Carnicer et al., Authentication of gold nanoparticle encoded pharmaceutical tablets using polarimetric signatures. Optics Letters 41, 4507-4510 (2016).
Shu, Catherine, TruTag raises $7.5 million Series C for tiny, edible barcodes that can be placed on pills, food and vaping systems, TechCrunch, Oct. 17, 2019.
De Jong et al., Drug delivery and nanoparticles: Applications and hazards. International Journal of Nanomedicine 3, 133-149 (2008).
Kumar et al., Genotoxic and carcinogenic potential of engineered nanoparticles: An update. Archives of Toxicology 87, 1883-1900 (2013).
Younes et al., Re-evaluation of silicon dioxide (E 551) as a food additive. EFSA Journal 16, 5088 (2018).
Kharraz et al., Optical delusions: A study of malicious QR codes in the wild. 2014 44th Annual IEEE/IFIP International Conference on Dependable Systems and Networks (DSN), 192-203 (2014).
Herder et al., Physical unclonable functions and applications: A tutorial. Proceedings of the IEEE 102, 1126-1141 (2014).
Gao et al., Emerging physical unclonable functions with nanotechnology. IEEE Access 4, 61-80 (2016).
Arppe et al., Physical unclonable functions generated through chemical methods for anti-counterfeiting. Nature Reviews Chemistry 1, 0031 (2017).
Mcgrath et al., A PUF taxonomy. Applied Physics Reviews 6, 011303 (2019).
Ruhrmair, Disorder-based security hardware: An overview. Security system design and trustable computing (eds. Chang, C. H. & Potkonjak, M.) pp. 3-37 (Springer, Switzerland, 2016).
Pappu et al., Physical one-way functions. Science 297, 2026-2030 (2002).
Horstmeyer et al., Physical key-protected one-time pad. Scientific Reports 3, 3543 (2013).
Goorden et al., Quantum-secure authentication of a physical unclonable key. Optica 1, 421-424 (2014).
Hu et al., Physically unclonable cryptographic primitives using self-assembled carbon nanotubes. Nature Nanotechnology 11, 559-565 (2016).
Cao et al., Optical identification using imperfections in 2D materials. 2D Materials 4, 045021 (2017).
Alharbi, A., Armstrong, D., Alharbi, S. & Shahrjerdi, D. Physically unclonable cryptographic primitives by chemical vapor deposition of layered MoS2. ACS Nano 11, 12772-12779 (2017).
Hwang et al., Nano-electromechanical switch based on a physical unclonable function for highly robust and stable performance in harsh environments. ACS Nano 11, 12547-12552 (2017).
Carro-Temboury et al., An optical authentication system based on imaging of excitation-selected lanthanide uminescence. Science Advances 4, e1701384 (2018).
Xiao et al., Direct Formation of Silk Nanoparticles for Drug Delivery. ACS Biomaterials Science & Engineering 2, 2050-2057 (2016).
Mwangi et al., Synthesis and characterization of silk fibroin microparticles for intra-articular drug delivery. International Journal of Pharmaceutics 485, 7-14 (2015).
Fei et al., Drug-laden 3D biodegradable label using QR code for anti-counterfeiting of drugs. Materials Science & Engineering C-Materials for Biological Applications 63, 657-662 (2016).
Altamimi et al., Anti-counterfeiting DNA molecular tagging of pharmaceutical excipients: An evaluation of lactose containing tablets. International Journal of Pharmaceutics 571, 118656 (2019).
Ilko et al., Tamper-proof tablets for distinction between counterfeit and originator drugs through PEG coding. European Journal of Pharmaceutics and Biopharmaceutics 99, 1-6 (2016).
Jeon et al., Cyber-Physical Watermarking with Inkjet Edible Bioprinting. Advanced Functional Materials, 2112479 (2022).
Ji et al., Encoding, Reading, and Transforming Information Using Multifluorescent Supramolecular Polymeric Hydrogels. Advanced Materials 30, 1705480 (2018).
Li et al., Photoresponsive Luminescent Polymeric Hydrogels for Reversible Information Encryption and Decryption. Advanced Science 6, 1901529 (2019).
Liu et al., Fluorescent Carbon- and Oxygen-Doped Hexagonal Boron Nitride Powders as Printing Ink for Anticounterfeit Applications. Advanced Optical Materials 7, 1901380 (2019).
Abdollahi et al., Photoluminescent and Chromic Nanomaterials for Anticounterfeiting Technologies: Recent Advances and Future Challenges. ACS Nano 14, 14417-14492 (2020).
Yang et al., Codes in Code: AIE Supramolecular Adhesive Hydrogels Store Huge Amounts of Information. Advanced Materials 33, 2105418 (2021).
Zhang et al., Materials and Technologies to Combat Counterfeiting of Pharmaceuticals: Current and Future Problem Tackling. Advanced Materials 32, 1905486 (2020).
You et al., Three-dimensional quick response code based on inkjet printing of upconversion fluorescent nanoparticles for drug anti-counterfeiting. Nanoscale 8, 10096-10104 (2016).
Liu et al., Aggregation-induced emission of a 2D protein supramolecular nanofilm with emergent functions. Materials Chemistry Frontiers 4, 1256-1267 (2020).
Nagarkar et al., Storing and Reading Information in Mixtures of Fluorescent Molecules. Acs Central Science 7, 1728-1735 (2021).
Wang et al., Fluorescent materials-based information storage. Materials Chemistry Frontiers 4, 1024-1039 (2020).
Ruggeri et al., A Multilayered Edible Coating to Extend Produce Shelf Life. ACS Sustainable Chemistry & Engineering 8, 14312-14321 (2020).
Leem et al., Photoelectric Silk via Genetic Encoding and Bioassisted Plasmonics. Advanced Biosystems 4, 2000040 (2020).
Leem et al., Edible Matrix Code with Photogenic Silk Proteins, ACS Central Science, Oct. 7 ,2021.
Mackey et al., A review of existing and emerging digital technologies to combat the global trade in fake medicines. Expert Opinion on Drug Safety 16, 587-602 (2017).
Sample, Fake drugs kill more than 250,000 children a year, doctors warn. The Guardian, Mar. 11, 2019.

(56) References Cited

OTHER PUBLICATIONS

Liang et al., Sexual medicine online risks to health-the problem of counterfeit drugs. Nature Reviews Urology 9, 480-482 (2012).
Clark, Rise in online pharmacies sees counterfeit drugs go global. Lancet 386, 1327-1328 (2015).
Blackstone et al., The health and economic effects of counterfeit drugs. American Health and Drug Benefits 7, 216-223 (2014).
Williams et al., The real impact of counterfeit medications. US Pharmacists 39, 44-46 (2014).
Fittler et al., A challenge for healthcare but just another opportunity for illegitimate online sellers: Dubious market of shortage oncology drugs. Plos One 13, e0203185 (2018).
Mackey et al., Digital danger: A review of the global public health, patient safety and cybersecurity threats posed by illicit online pharmacies. British Medical Bulletin 118, 115-131 (2016).
Venhuis et al.,Oncology drugs in the crosshairs of pharmaceutical crime. Lancet Oncology 19, E209-E217 (2018).
Kovacs et al., Technologies for detecting falsified and substandard drugs in low and middle-income countries. Plos One 9, e90601 (2014).
Davison Pharmaceutical anti-counterfeiting: Combating the real danger from fake drugs. John Wiley & Sons, Inc., New Jersey (2011).
Shanley, Anticounterfeiting: In search of the unhackable. Pharmaceutical Technology 42, 56-58 (2018).
Huang et al., Unbreakable codes in electrospun fibers: Digitally encoded polymers to stop medicine counterfeiting. Advanced Materials 22, 2657-2661 (2010).
Han et al., Lithographically encoded polymer microtaggant using high-capacity and error-correctable QR code for anti-counterfeiting of drugs. Advanced Materials 24, 5924-5929 (2012).
Bae et al., Self-organization of maze-like structures via guided wrinkling. Science Advances 3, e1700071 (2017).
Edinger et al., QR encoded smart oral dosage forms by inkjet printing. International Journal of Pharmaceutics 536, 138-145 (2018).
Rehor et al., Biodegradable microparticles for simultaneous detection of counterfeit and deteriorated edible products. Small 13, 1701804 (2017).
Kim et al., Porous microwells for geometry-selective, large-scale microparticle arrays. Nature Materials 16, 139-146 (2017).
Smith et al., Plasmonic nanoparticles as a physically unclonable function for responsive anti-counterfeit hanofingerprints. Advanced Functional Materials 26, 1315-1321 (2016).
Arppe-Tabbara et al., Versatile and validated optical authentication system based on physical unclonable functions. ACS Applied Materials & Interfaces 11, 6475-6482 (2019).
Wali et al., Biological physically unclonable function. Communications Physics 2, 39 (2019).
Mariani et al., Biomaterials: Foreign bodies or tuners for the immune response?. International Journal of Molecular Sciences 20, 636 (2019).
Rockwood et al., Materials fabrication from Bombyx mori silk fibroin. Nature Protocols 6, 1612-1631 (2011).
Thurber et al., In vivo bioresponses to silk proteins. Biomaterials 71, 145-157 (2015).
Choi et al., Anderson light localization in biological nanostructures of native silk. Nature Communications 9, 452 (2018).
Leem et al., Scalable and continuous nanomaterial integration with transgenic fibers for enhanced photoluminescence. Materials Horizons 4, 281-289 (2017).
Leem et al., Green-light-activated photoreaction via genetic hybridization of far-red fluorescent protein and silk. Advanced Science 5, 1700863 (2018).
Kim et al., Dissolvable films of silk fibroin for ultrathin conformal bio-integrated electronics. Nature Materials 9, 511-517 (2010).
Qi et al., A review of structure construction of silk fibroin biomaterials from single structures to multi-level structures. International Journal of Molecular Sciences 18, 237 (2017).
Cao et al., Biodegradation of silk biomaterials. International Journal of Molecular Sciences 10, 1514-1524 (2009).
Marelli et al., Silk fibroin as edible coating for perishable food preservation. Scientific Reports 6, 25263 (2016).
Tao et al., Silk-based conformal, adhesive, edible food sensors. Advanced Materials 24, 1067-1072 (2012).
Lievens et al., Genetically modified animals: Options and issues for traceability and enforcement. Trends in Food Science & Technology 44, 159-176 (2015).
Richards et al., Safety assessment of recombinant green fluorescent protein orally administered to weaned rats. Journal of Nutrition 133, 1909-1912 (2003).
Jang et al., Single-dose oral toxicity study of genetically modified silkworm expressing EGFP protein in ICR mouse. Korean Journal of Agricultural Science 43, 109-115 (2016).
Kim et al., Novel fabrication of fluorescent silk utilized in biotechnological and medical applications. Biomaterials 70, 48-56 (2015).
Kim et al., Precisely printable and biocompatible silk fibroin bioink for digital light processing 3D printing. Nature Communications 9, 1620 (2018).
Tamura et al., Germline transformation of the silkworm *Bombyx mori* L. using a piggyBac transposon-derived vector. Nature Biotechnology 18, 81-84 (2000).
Teule et al., Silkworms transformed with chimeric silkworm/spider silk genes spin composite silk fibers with improved mechanical properties. Proceedings of the National Academy of Sciences of the United States of America 109, 923-928 (2012).
Iizuka et al., Colored fluorescent silk made by transgenic silkworms. Advanced Functional Materials 23, 5232-5239 (2013).
Ostoja-Starzewski, Random-fields and processes in mechanics of granular-materials. Mechanics of Materials 16, 55-64 (1993).
Duran, Sands, powders and grains. An introduction to the physics of granular materials. (Springer-Verlag, New York, 2000).
Maiti et al., A systematic method to evaluate and compare the performance of physical unclonable functions. Embedded systems design with FPGAs. pp. 245-267 (Springer-Verlag, New York, 2013).
Suh et al., Physical unclonable functions for device authentication and secret key generation. 2007 44th ACM/IEEE Design Automation Conference, vols. 1 and 2, 9-14 (2007).
Che et al., Analysis of entropy in a hardware-embedded delay PUF. Cryptography 1, 8 (2017).
Gong et al., Pitfall of the strongest cells in static random access memory physical unclonable functions. Sensors 18, 1776 (2018).
Han et al., Quantum-dot-tagged microbeads for multiplexed optical coding of biomolecules. Nature Biotechnology 19, 631-635 (2001).
Nagy et al., Thermal stability of chemically denatured green fluorescent protein (GFP)—A preliminary study. Thermochimica Acta 410, 161-163 (2004).
Alkaabi et al., Effect of pH on thermal- and chemical-induced denaturation of GFP. Applied Biochemistry and Biotechnology 126, 149-156 (2005).
Tao et al., Silk materials—A road to sustainable high technology. Advanced Materials 24, 2824-2837 (2012).
Valsesia et al., User Authentication via PRNU-Based physical unclonable functions. IEEE Translations on Information Forensics and Security 12, 1941-1956 (2017).
Leem et al., Edible unclonable functions. Nature Communications 11, 328 (2020).
Bakan et al., Invisible Thin-Film Patterns with Strong Infrared Emission as an Optical Security Feature. Advanced Optical Materials 6, 1800613 (2018).
Trenfield et al., Track-and-trace: Novel anti-counterfeit measures for 3D printed personalized drug products using smart material inks. International Journal of Pharmaceutics 567, 118443 (2019).
Ludasi et al., Anti-counterfeiting protection, personalized medicines—Development of 2D identification methods using laser technology. International Journal of Pharmaceutics 605, 120793 (2021).
Hall, Technology for combating counterfeit medicine. Pathogens and Global Health 106, 73-76 (2012).

\* cited by examiner

SEQUENCE LISTING

<160> NUMBER OF SEQ ID NOS: 1

<210> SEQ ID NO 1
<211> LENGTH: 717
<212> TYPE: PRT
<213> ORGANISM: silkworm

<400> SEQUENCE: 1

```
Asp Ala Ser Gly Ala Val Ile Glu Glu Gln Ile Thr Thr Lys Lys Asn
1               5                   10                  15

His Gly Ile Leu Gly Lys Asn Glu Lys Thr Phe Val Ile Thr Thr Asp
            20                  25                  30

Ser Asp Gly Asn Glu Ser Ile Val Glu Glu Asp Val Leu Met Lys Met
        35                  40                  45

Val Ser Glu Leu Ile Lys Glu Asn Met His Met Lys Leu Tyr Met Glu
50                  55                  60

Gly Thr Val Asn Asn His His Phe Lys Cys Thr Ser Glu Gly Glu Gly
65                  70                  75                  80

Lys Pro Tyr Glu Gly Thr Gln Thr Met Arg Ala Val Glu Gly Gly Pro
            85                  90                  95

Leu Pro Phe Ala Phe Asp Ile Leu Ala Thr Ser Phe Met Tyr Gly Ser
            100                 105                 110

Lys Val Thr Thr Tyr Glu Asp Gly Gly Val Leu Thr Ala Thr Gln Asp
            115                 120                 125

Thr Ser Leu Gln Asp Gly Cys Leu Ile Tyr Asn Val Lys Ile Arg Gly
130                 135                 140

Val Asn Phe Pro Ser Asn Gly Pro Val Met Gln Lys Lys Thr Leu Gly
145                 150                 155                 160

Trp Glu Ala Ser Thr Glu Thr Leu Tyr Pro Ala Asp Gly Gly Leu Glu
                165                 170                 175

Gly Arg Met Pro Gly Val Tyr Tyr Val Asp Arg Arg Glu Ala Asp Lys
            180                 185                 190

Glu Thr Tyr Val Glu Gln His Glu Val Ala Val Ala Arg Tyr Cys Asp
            195                 200                 205

Leu Pro Ser Lys Leu Gly His Arg Pro Gln Gln Val Asp Ser Val Ser
    210                 215                 220

Tyr Gly Ala Gly Arg Gly Tyr Gln Gly Ala Gly Ser Ala Ala Ser
225                 230                 235                 240

Ser Val Ser Ser Ala Ser Ser Arg Ser Tyr Asp Tyr Ser Arg Arg Lys
                245                 250                 255

Asn Cys Gly Ile Pro Arg Met Arg Val Lys Thr Phe Val Ile Leu Cys
            260                 265                 270

Cys Ala Leu Gln Tyr Val Ala Tyr Thr Asn Ala Asn Ile Asn Asp Phe
            275                 280                 285

Asp Glu Asp Tyr Phe Gly Ser Asp Val Thr Val Gln Ser Ser Asn Thr
            290                 295                 300

Thr Asp Glu Ile Ile Arg Asp Ala Ser Gly Ala Val Ile Glu Glu Gln
305                 310                 315                 320

Ile Thr Thr Lys Lys Met Gln Arg Lys Asn Lys Asn His Gly Ile Leu
                325                 330                 335

Gly Lys Asn Glu Lys Met Ile Lys Thr Phe Val Ile Thr Thr Asp Ser
            340                 345                 350

Asp Gly Asn Glu Ser Ile Val Glu Glu Asp Val Leu Met Lys Thr Leu
            355                 360                 365
```

```
Ser Asp Gly Thr Val Ala Gln Ser Tyr Val Ala Ala Asp Ala Gly Ala
    370                 375                 380

Tyr Ser Gln Ser Gly Pro Tyr Val Ser Asn Ser Gly Tyr Ser Thr His
385                 390                 395                 400

Gln Gly Tyr Thr Ser Asp Phe Ser Thr Ser Ala Ala Val Gly Ala Gly
                405                 410                 415

Ser Ser Gly Arg Met Val Ser Glu Leu Ile Lys Glu Asn Met His Met
                420                 425                 430

Lys Leu Tyr Met Glu Gly Thr Val Asn Asn His His Phe Lys Cys Thr
            435                 440                 445

Ser Glu Gly Glu Gly Lys Pro Tyr Glu Gly Thr Gln Thr Met Arg Ile
450                 455                 460

Lys Ala Val Glu Gly Gly Pro Leu Pro Phe Ala Phe Asp Ile Leu Ala
465                 470                 475                 480

Thr Ser Phe Met Tyr Gly Ser Lys Thr Phe Ile Asn His Thr Gln Gly
                485                 490                 495

Ile Pro Asp Phe Phe Lys Gln Ser Phe Pro Glu Gly Phe Thr Trp Glu
            500                 505                 510

Arg Val Thr Thr Tyr Glu Asp Gly Gly Val Leu Thr Ala Thr Gln Asp
            515                 520                 525

Thr Ser Leu Gln Asp Gly Cys Leu Ile Tyr Asn Val Lys Ile Arg Gly
530                 535                 540

Val Asn Phe Pro Ser Asn Gly Pro Val Met Gln Lys Lys Thr Leu Gly
545                 550                 555                 560

Trp Glu Ala Ser Thr Glu Thr Leu Tyr Pro Ala Asp Gly Gly Leu Glu
                565                 570                 575

Gly Arg Ala Asp Met Ala Leu Lys Leu Val Gly Gly Gly His Leu Ile
            580                 585                 590

Cys Asn Leu Lys Thr Thr Tyr Arg Ser Lys Pro Ala Lys Asn Leu
            595                 600                 605

Lys Met Pro Gly Val Tyr Tyr Val Asp Arg Arg Leu Glu Arg Ile Lys
610                 615                 620

Glu Ala Asp Lys Glu Thr Tyr Val Glu Gln His Glu Val Ala Val Ala
625                 630                 635                 640

Arg Tyr Cys Asp Leu Pro Ser Lys Leu Gly His Arg Pro Gln Gln Val
            645                 650                 655

Asp Ser Val Ser Tyr Gly Ala Gly Arg Gly Tyr Gly Gln Gly Ala Gly
            660                 665                 670

Ser Ala Ala Ser Ser Val Ser Ser Ala Ser Ser Arg Ser Tyr Asp Tyr
            675                 680                 685

Ser Arg Arg Asn Val Arg Lys Asn Cys Gly Ile Pro Arg Arg Gln Leu
    690                 695                 700

Val Val Lys Phe Arg Ala Leu Pro Cys Val Asn Cys Asn
705                 710                 715
```

EDIBLE UNCLONABLE FUNCTIONS

CROSS-REFERENCE TO RELATED APPLICATIONS

The present patent application is a 35 U.S.C. § 371 Nationalization Application of and claims the priority benefit of the International Patent Application Serial No. PCT/US20/46580 filed Aug. 15, 2020, which is related to and claims the priority benefit of U.S. Provisional Patent Application Ser. No. 62/915,667 filed 16 Oct. 2019 entitled "EDIBLE UNCLONABLE FUNCTIONS", and U.S. Provisional Patent Application Ser. No. 62/915,666 filed 16 Oct. 2019 entitled "IMAGE PROCESSING AND AUTHENTICATION OF EDIBLE UNCLONABLE FUNCTIONS", the contents of each of which are hereby incorporated by reference in its entirety into the present disclosure.

STATEMENT REGARDING GOVERNMENT FUNDING

This invention was made with government support under FA2386-17-1-4072 awarded by US Air Force Office of Scientific Research. The government has certain rights in the invention.

TECHNICAL FIELD

The present disclosure generally relates to counterfeit measures, and in particular, to an arrangement concerning an edible unclonable function counterfeit measure.

BACKGROUND

This section introduces aspects that may help facilitate a better understanding of the disclosure. Accordingly, these statements are to be read in this light and are not to be understood as admissions about what is or is not prior art.

Counterfeit medicines have become ubiquitous, presenting myriad problems. This problem of counterfeit medicines is not a new one, but is becoming a tremendous burden to society in all countries. While 'fake' pharmaceutical products can be explicitly categorized into a plurality of categories including substandard, falsified, counterfeit, and diverted ones, they are all often referred to, as a single group, counterfeit medicines. They pose a significant threat to patient safety and public health as well as cause heavy economic losses in developed and less developed countries. As a devastating example, counterfeit drugs for malaria and pneumonia treatments cause estimated 250,000 child deaths each year. Counterfeit medicines of both lifestyle drugs (e.g. treatments for erectile dysfunction) and lifesaving drugs (e.g. treatments for cancer, malaria, diabetes, etc.) are increasingly being produced in developed and developing countries, in part due to the increased public use of online pharmacies. In addition, as an infringement of intellectual properties, scientific innovations and financial rewards in pharmaceutical companies are undermined by the widespread counterfeiting of medicine. The health and economic consequences of counterfeit medicines are far more serious in low- and middle-income countries. It is estimated that counterfeit medicines account for 10% of the global pharmaceutical trade and more than 20-30% of all medicines in Africa, Asia, and the Middle East.

There are a variety of approaches for detecting counterfeit medicines and for offering possible solutions for reducing the threat. Traditionally, analytical chemistry and spectroscopy technologies have been used to identify counterfeit medicines by detecting chemical signatures of major ingredients. However these techniques require sophisticated and expensive machines and have limited accuracy based on recognizing of such main ingredients. Other techniques include marking and printing on the medicine surface at various levels of resolution using lasers and other proprietary technologies, which modify the outer surface or coating of tablets or capsules, however, this technique is prone to duplication by counterfeiters. Recently, digital anti-counterfeit technologies have played a more significant role in authentication and supply chain. Package-level barcodes and radio frequency identification (RFID) are commonly used for instantaneous remote authentication. Several mobile technologies have been introduced for authentication services, track and trace solutions, and medicine recognitions. Detrimentally, such authentication and security techniques are symmetric; that is, if illegitimate manufacturers or sellers have access to the same techniques, it would be possible for them to create clones. An ideal authentication technology should be asymmetric with a form of on-dose authentication which can be directly swallowed and digestible. Specifically, on-dose (or in-dose) authentication means that every individual pill or dose is verified as genuine in the absence of packaging. Even if the original packaging is not retained by pharmacists or patients, the possibility of ingestion of counterfeit medicines is substantially eliminated. Indeed, the packaging information is often unavailable; pills are sold in small quantities and individual strips dispensed by pharmacists. On-dose authentication maximally reduces the opportunity for illegitimate sellers to use expired, counterfeit, or substandard drugs.

In this respect, a few promising technologies have recently been introduced with the potential of digital authentication, including digitally encoded polymers, QR-coded microtaggants and advanced wrinkle-based tags, QR code printing of active pharmaceutical ingredients, encoded-multifunctional hydrogel microparticles, large-scale microparticle arrays, encoded metal nanomaterials, and silica microtags. However, such materials are often not ideal from an oral intake safety perspective. These approaches rely on biocompatible and biodegradable yet exogenous materials, such as polystyrene, cellulose-acetate-phthalate (CAP), poly(lactic-co-glycolic acid) (PLGA), poly(ethylene glycol) (PEG), poly(ethylene glycol) diacrylate (PEGDA), silver, gold, and silica. It should be noted that foreign and nano-sized food additives could potentially have hazardous and adverse (e.g. carcinogenic and cytotoxic) effects, which currently have resulted in limited utilizations. In addition, such simple tagging technologies could be vulnerable to attackers, due to the limited security level.

Therefore, there is an unmet need for a novel approach to provide unclonable security for pharmaceuticals to combat the widespread availability of counterfeits.

SUMMARY

A method of generating a physically unclonable function for pharmaceutical authentication is disclosed. The method includes generating an edible physically unclonable function (PUF), affixing the edible PUF onto a pharmaceutical in a random distribution, and generating a cryptographic key based on the randomly distributed and affixed edible PUF.

According to one embodiment in the above method, the edible PUF comprises silk proteins.

According to one embodiment in the above method, the edible PUF comprises edible polymers.

According to one embodiment in the above method, the edible PUF is based on randomly distributed edible fluorescent proteins.

According to one embodiment in the above method, the edible PUF is based on randomly distributed edible fluorescent dyes.

According to one embodiment in the above method, the edible PUF is based on randomly distributed fluorescent protein-expressed silk particles.

According to one embodiment in the above method, the edible PUF is based on randomly distributed edible fluorescent dye-containing edible polymer particles.

According to one embodiment in the above method, the fluorescent protein-expressed silk can be produced by transgenesis of genetically engineered domesticated silkworms.

According to one embodiment in the above method, the transgenes is expressed by germline transformation using gene splicing.

According to one embodiment in the above method, the gene splicing is based on piggyBac.

According to one embodiment in the above method, the fluorescent silk protein is selected from the group consisting of enhanced cyan fluorescent protein (eCFP), enhanced green fluorescent protein (eGFP), enhanced yellow fluorescent protein (eYFP), and mKate2 (far-red) fluorescent protein.

According to one embodiment in the above method, the edible polymers are selected from the group consisting of Starch, cellulose derivatives, chitosan, pectin, alginates, gums, carrageenans, and combinations thereof.

According to one embodiment in the above method, the edible polymers are selected from the group consisting of gelatin, collagen, albumin, milk protein, and combinations thereof.

According to one embodiment in the above method, the edible polymers are selected from the group consisting of zein, soy, wheat gluten, lectins, and combinations thereof.

According to one embodiment in the above method, the edible polymers are selected from the group consisting of Fatty acids, triglycerides, phospholipids, and combinations thereof.

According to one embodiment in the above method, the edible fluorescent proteins are selected the group consisting of red fluorescent protein (DsRed), orange fluorescent protein (mKO), and a combination thereof.

According to one embodiment in the above method, the edible fluorescent dyes are selected from the group consisting of Brilliant Blue FCF, Indigotine, Fast Green FCF, Erythrosine, Allura Red AC, Tartrazine, Sunset Yellow FCF, and combinations thereof.

A method of fabricating and applying a physically unclonable function to a pharmaceutical is also disclosed. The method includes constructing plasmid vector DNA for silkworm transgenesis to thereby generate one or more fluorescent silk proteins. The method also includes removing sericin from the one or more fluorescent silk proteins. Furthermore, the method includes cutting the sericin-removed one or more fluorescent silk proteins into a plurality of pieces. Additionally, the method includes cleaning the cut pieces with a solution, filtering the dissolved solution, dialyzing the filtered dissolved solution, and centrifuging the dialyzed solution to thereby provide a regenerated silk fibroin solution. In addition, the method includes freeze-drying the regenerated silk fibroin solution, mechanically grinding the freeze-dried silk fibroin into granular silk microparticles, sieving the mechanically ground silk fibroin to generate fluorescent silk microparticles, and generating an admixture of the fluorescent silk microparticles. Furthermore, the method includes broadcasting the admixture of the fluorescent silk microparticles to the surface of a polystyrene Petri dish thereby generating a silk film that are adapted to be attached to a pharmaceutical.

According to one embodiment in the above method, the one or more fluorescent silk proteins include eCFP, eGFP, eYFP, and mKate2.

According to one embodiment in the above method, the cleaning of the one or more fluorescent silk proteins is in a mixture solution of $Na_2CO_3$ (0.2%) at temperatures lower than 50° C.

According to one embodiment in the above method, the cut sericin-removed one or more fluorescent silk proteins range from about 2 mm to about 5 mm.

According to one embodiment in the above method, the cut pieces are dissolved in an aqueous solution of LiBr (9.5 M) at 45° C. for four hours with stirring of 400 rpm.

According to one embodiment in the above method, the dissolved solution was filtered through a miracloth.

According to one embodiment in the above method, the filtered solution was dialyzed in deionized water at room temperature for about two days with a cellulose semipermeable tube to remove the LiBr.

According to one embodiment in the above method, the centrifuging of the dialyzed solution is with a speed of 9000 rpm at about 4° C. for about 20 minutes to thereby form the regenerated silk fibroin solution.

According to one embodiment in the above method, the regenerated silk fibroin solutions were freeze-dried at about −18° C. for seven days.

According to one embodiment in the above method, the freeze-dried fluorescent silk was mechanically ground into the granular microparticles with one of a mortar and pestle, a powered blender, or a combination thereof.

According to one embodiment in the above method, the sieving generates fluorescent silk microparticles with a predetermined size range by shaking the fluorescent silk microparticles through a stack of two standard test sieves with corresponding opening.

According to one embodiment in the above method, the fluorescent silk microparticles are mixed at a ratio of 1:1:1:1 (eCFP, eGFP, eYFP, and mKate2 silk) in a microcentrifuge tube and then shaken by hand.

According to one embodiment in the above method, the broadcasting of the admixture of the fluorescent silk microparticles to the surface of a polystyrene Petri dish is through a sieve with a predetermined opening size by mechanical shaking.

DETAILED DESCRIPTION

Figure 1A:
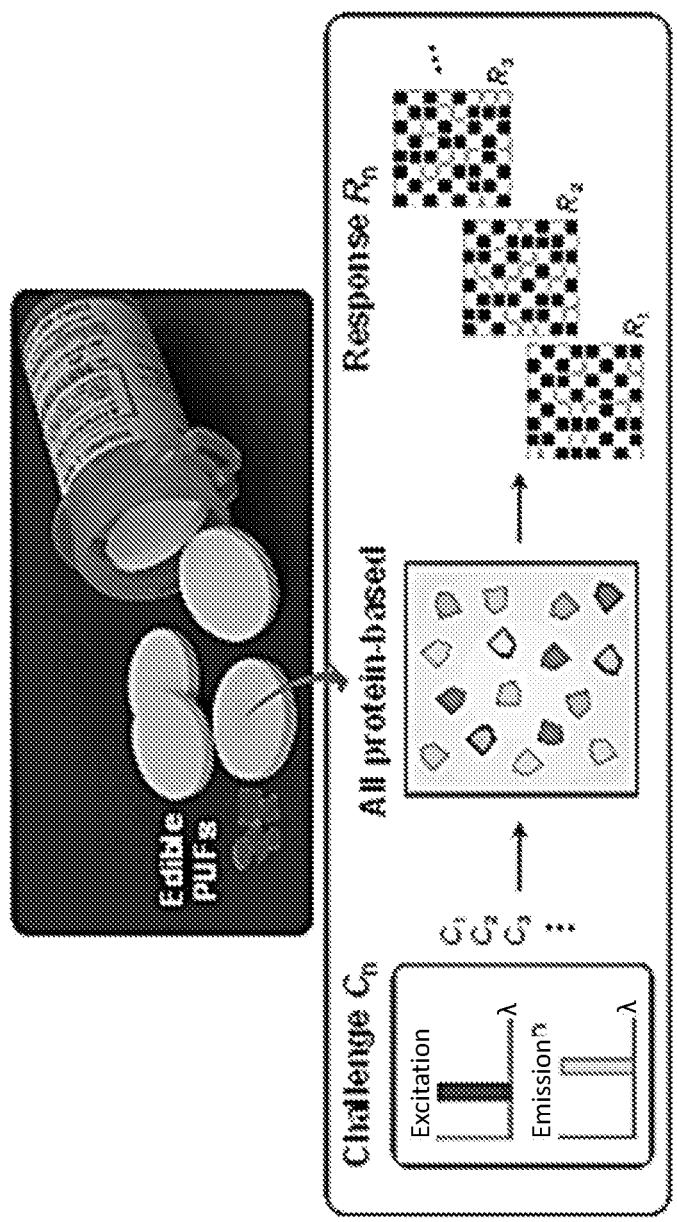
FIG. 1a is a schematic of application of an edible physically unclonable functions (PUFs) for use with pharmaceuticals.

The patent or application file contains at least one drawing executed in color. Copies of this patent or patent application publication with color drawing(s) will be provided by the Office upon request and payment of the necessary fee.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

One excellent way for guaranteeing high security of on-dose authentication and protection against counterfeiting medicines is to utilize physically unclonable functions (PUFs). A PUF depends on the uniqueness of its physical microstructure that defines the PUF. This uniqueness depends on a myriad random physical factors introduced during manufacturing; and given that these factors are unpredictable and uncontrollable, duplication is substantially impossible. A PUF does not use a single encryption key that can possible be decoded and used without authorization. Instead, a PUF implements a challenge-response authentication to authenticate the associated microstructure. When a physical stimulus is applied to the structure, while it reacts in an unpredictable way, it reacts in a repeatable fashion. The applied stimulus is called a challenge, and the reaction of the PUF is called the associated response. Such a specific challenge and its corresponding response are held in a secure database, and thus authentication can be checked against such a database. The challenge-response and its communication with the secured database can be encrypted for added security.

Importantly, PUFs can be asymmetric such that it is easy to make a PUF, but is extremely challenging for counterfeiters to create a clone. Once an output response is read from the database, it cannot be re-used as well. The information on dose, frequency, and caution can be encoded for user adherence by labeling individual medicines.

For digital on-dose PUFs, the present disclosure presents silk proteins and fluorescent proteins as edible and digestible photonic biomaterials. From an edible perspective, important considerations include digestibility and nonallergenic properties. To this end, endogenous natural materials or biomaterials are chosen for on-dose applications. Importantly, silk proteins (i.e. fibroin) have excellent intrinsic functionality, biocompatibility, and low immunogenicity with minimal inflammatory and immune responses. Naturally-derived silk fibroin, without any external treatment, are dissolved in an aqueous solution. Silk proteins are also degradable and the degradation rate is controllable by using different silk regeneration and fabrication methods. More relevantly, silk proteins are edible and digestible. In addition, fluorescent proteins have been introduced into the food supply from genetically modified food. The potential toxicity and allergenicity are minimal with ingestion of green fluorescent protein. When compared with common food allergens, fluorescent proteins do not have common allergen epitopes and are degraded during gastric digestion. From an engineering perspective, processing of silk proteins is readily available for constructing structures and patterns from nanoscale to microscale. In particular, the polymeric nature from silk proteins can easily be fabricated into a variety of types of rigid or flexible structures with tunable mechanical and optical properties. Furthermore, silk proteins containing recombinant fluorescent proteins can be produced by transgenesis of genetically engineered domesticated silkworms. Transgenes of a variety of fluorescent proteins can be expressed by germline transformation using the gene splicing piggyBac method. The hybridization method can yield transformed silkworms with multiple successive generations and produce fluorescent silk in large amounts.

To this end, the present disclosure provides all protein-based PUFs that generate cryptographic keys with interactive multiple challenge-response pairs for on-dose authentication and anti-counterfeiting of medicines. The edible PUFs are made from silk (i.e. *Bombyx mori*) protein microparticles that are genetically fused with different fluorescent proteins, including enhanced cyan fluorescent protein (eCFP), enhanced green fluorescent protein (eGFP), enhanced yellow fluorescent protein (eYFP), and mKate2 (far-red) fluorescent protein. Particulate fluorescent silk is embedded in a thin film of natural white silk proteins, which can be directly attached onto the surface of a medicine in a solid oral dosage form. The source of entropy is a randomly scattered (or broadcast) fluorescent microparticle admixture of eCFP, eGFP, eYFP, and mKate2 silk, as the behavior of granular or particulate materials intrinsically has complex spatiotemporal fluctuations during the fabrication process. For the challenge-response requirement of PUFs, a unique set of excitation and emission bands of different fluorescent proteins serves as input challenges. The edible PUFs produce genuinely inherent output response images of spontaneous emission (i.e. fluorescence). The reported PUFs have strong randomness that guarantees unique and unpredictable cryptographic keys with a relatively large encoding capacity. We further characterize the fundamental PUF functions, including uniformity, uniqueness (for security), and reproducibility (for reliability), by calculating inter-device Hamming Distances (HDs), intra-device HDs, false positive rates, and false negative rates. The reported protein-based PUFs can provide an immediate solution with high security for on-dose authentication and anti-counterfeiting of medicines.

Fluorescent silk produced by the genetic fusion of fluorescent proteins (i.e. eCFP, eGFP, eYFP, and mKate2) via germline transformation (i.e. piggyBac transposon) and natural white silk were utilized. The following chemicals were used; dialysis tube (pore size 12,000 Da MWCO), lithium bromide (LiBr, ≥99%), miracloth (pore size 22-25 μm), sodium carbonate ($Na_2CO_3$, ≥99%), and Triton X100, purchased from Sigma-Aldrich Co. (Milwaukee, WI, USA). To select appropriate particle sizes and to broadcast fluorescent silk microparticles, we used two standard test sieves with opening sizes of 90 (No. 170) and 106 (No. 140) μm, purchased from Cole-Parmer (Niles, IL, USA). All experiments were performed under the ambient conditions (22±2° C. and 40±10% relative humidity). It should be noted that any organic solvents and synthetic polymers were completely avoided for edibility and safe consumption.

A variety of image processing techniques can be used to extract information from the PUF and to securely check against the database for authentication. One such novel technique is described in the sister patent application filed on the same day as the instant patent application, entitled: IMAGE PROCESSING AND AUTHENTICATION OF UNCLONABLE FUNCTIONS.

Figure 1B:
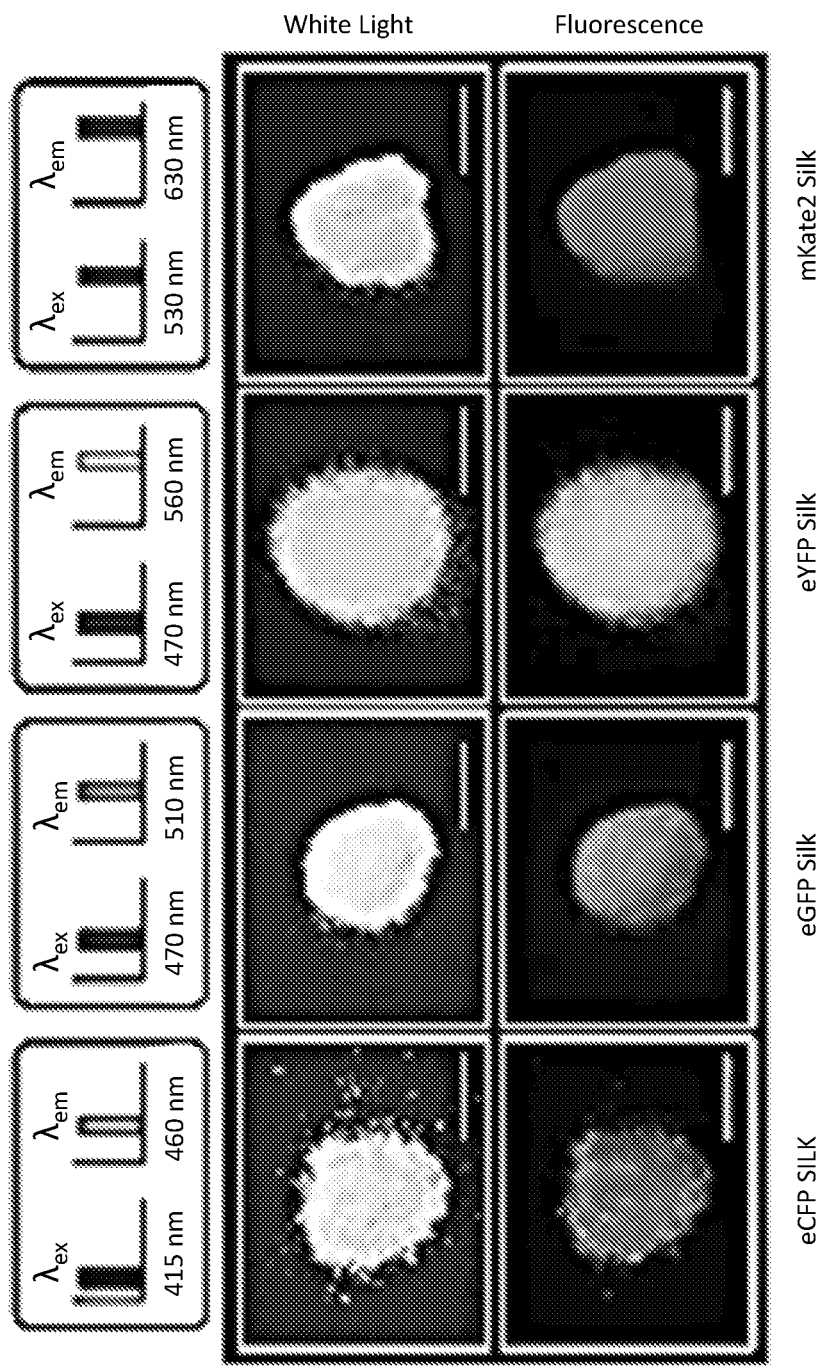
FIG. 1b shows schematics of photoluminescent properties of fluorescent silk proteins that are used to realize multiple challenge-response pairs in an edible PUF platform for heightened security according to the present disclosure.
Figure 1C:
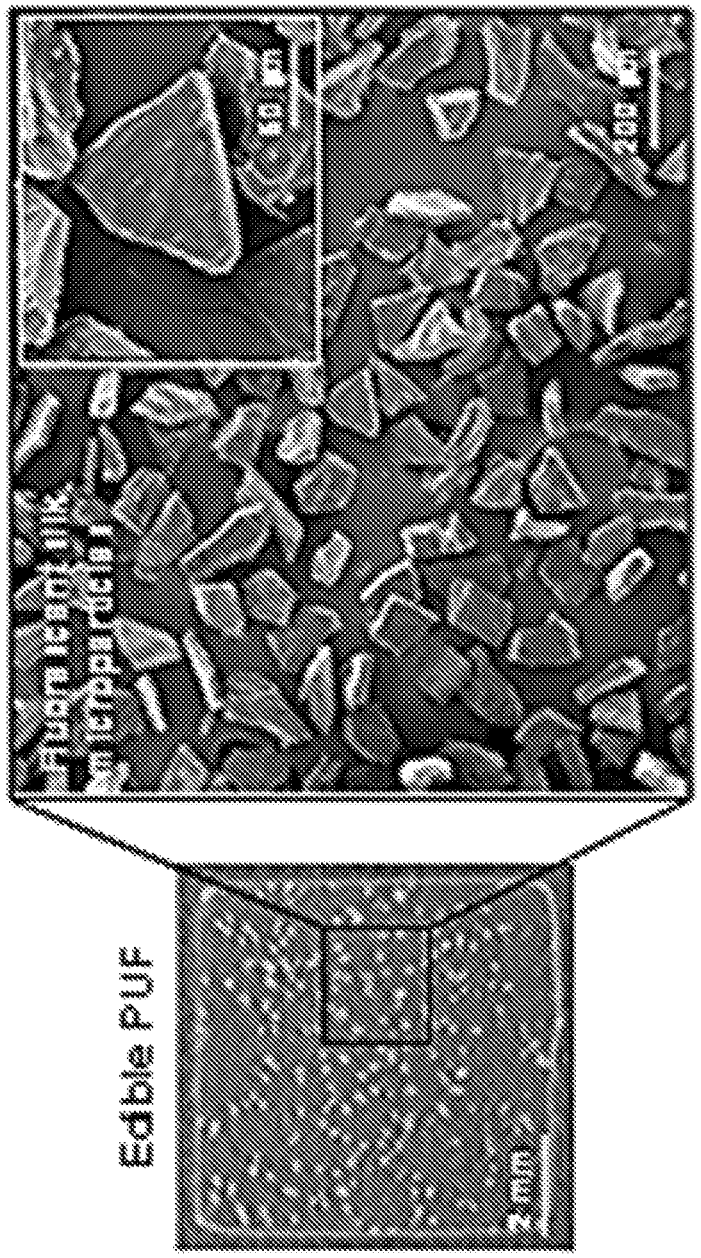
FIG. 1c is a scanning electron microscope (SEM) output of an edible PUF device in which fluorescent silk microparticles are embedded in a thin silk film.
Figure 1D:
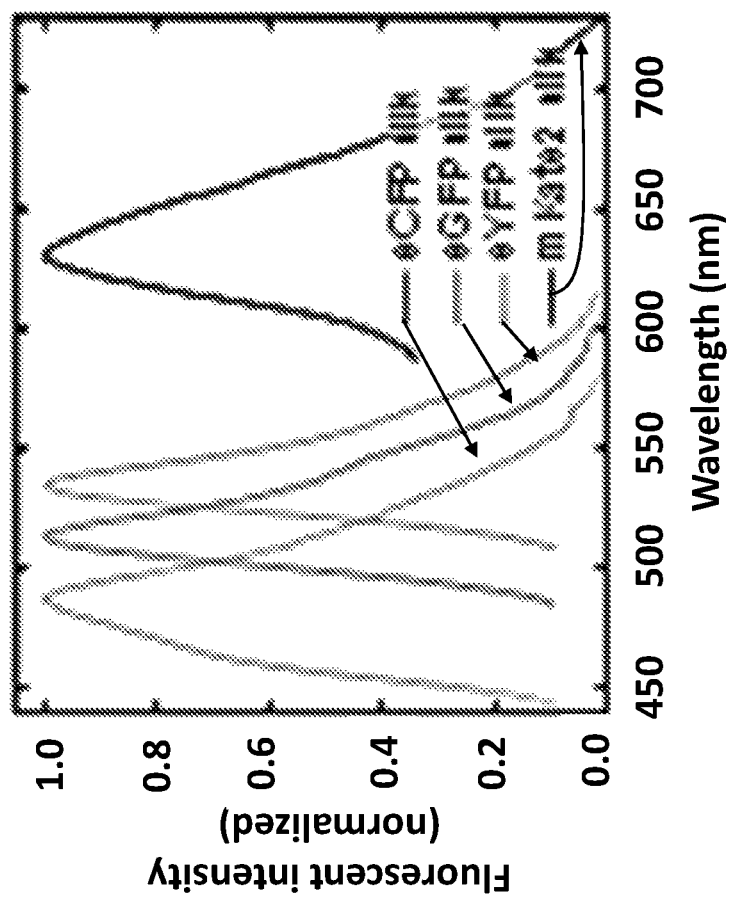
FIG. 1d is an emission spectra of particulate eCFP, eGFP, eYFP and mKate2 silk which cover a relatively broad wavelength range in the visible light, while the emission peak positions are not overlapped among others.
Figure 1E:
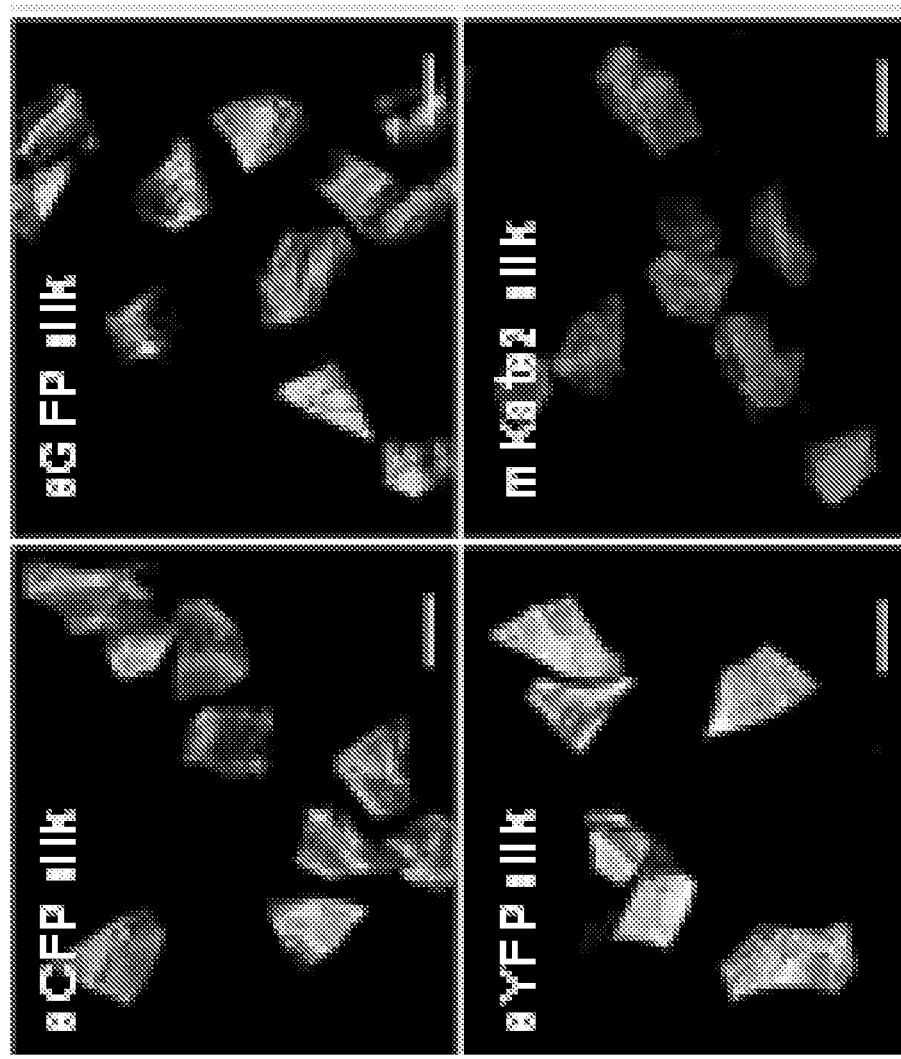
FIG. 1e provides confocal fluorescence microscopy images of the corresponding fluorescent silk microparticles under excitation of 405, 458, 514, or 561 nm for eCFP, eGFP, eYFP and mKate2 silk, respectively.

Referring to FIG. 1a, a schematic of edible PUFs for use with pharmaceuticals is shown. FIG. 1a shows a schematic illustration of an on-dose PUF with a photograph of covert and transparent PUFs attached on the surface of medicines. The PUF device is composed of proteins from fluorescent proteins and silk that are edible and digestible. The distinct photoluminescent properties of fluorescent proteins in silk provide the parametric support of unique challenge-response pairs. In reaction by an input challenge, the edible PUF generates its corresponding output response. FIG. 1b shows that the photoluminescent properties of fluorescent silk proteins are used to realize multiple challenge-response pairs in an edible PUF platform for heightened security. FIG. 1c is a photograph of an edible PUF device in which fluorescent silk microparticles are embedded in a thin silk film. SEM image of fluorescent silk microparticles with zeolite-like shapes is shown. FIG. 1d is an emission spectra of particulate eCFP, eGFP, eYFP and mKate2 silk which cover a relatively broad wavelength range in the visible light, while the emission peak positions are not overlapped among others. FIG. 1e are confocal fluorescence microscopy images of the corresponding fluorescent silk microparticles under excitation of 405, 458, 514, or 561 nm. The scale bar is 100 μm. The size of fluorescent silk microparticles is 99.3±7.9 μm (mean±standard deviation). Importantly, challenge-response pairs differentiate the protein-based PUFs of the present disclosure from other common unique objects and tags. In reaction to optical challenges, defined by a unique set of excitation and emission bands of different fluorescent proteins, the edible PUF made of silk protein (i.e. fibroin) and fluorescent proteins generates distinct output responses. The source of entropy is randomly distributed fluorescent silk microparticles seamlessly embedded in a covert thin transparent silk film. First, we take advantage of four different fluorescent proteins (i.e. eCFP, eGFP, eYFP, and mKate2) that have specific excitation and emission peaks in the visible wavelength range (provided in Table 1).

TABLE 1

Optical properties of fluorescent proteins genetically hybridized with silk

| Fluorescent protein | Excitation maximum (nm) | Emission maximum (nm) | Extinction coefficient ($M^{-1} cm^{-1}$) | Quantum yield (%) |
| --- | --- | --- | --- | --- |
| eCFP | 434 | 477 | 32,500 | 40 |
| eGFP | 489 | 509 | 55,000 | 60 |
| eYFP | 514 | 527 | 84,000 | 61 |
| mKate2 | 588 | 633 | 62,500 | 40 |

Figure 2:
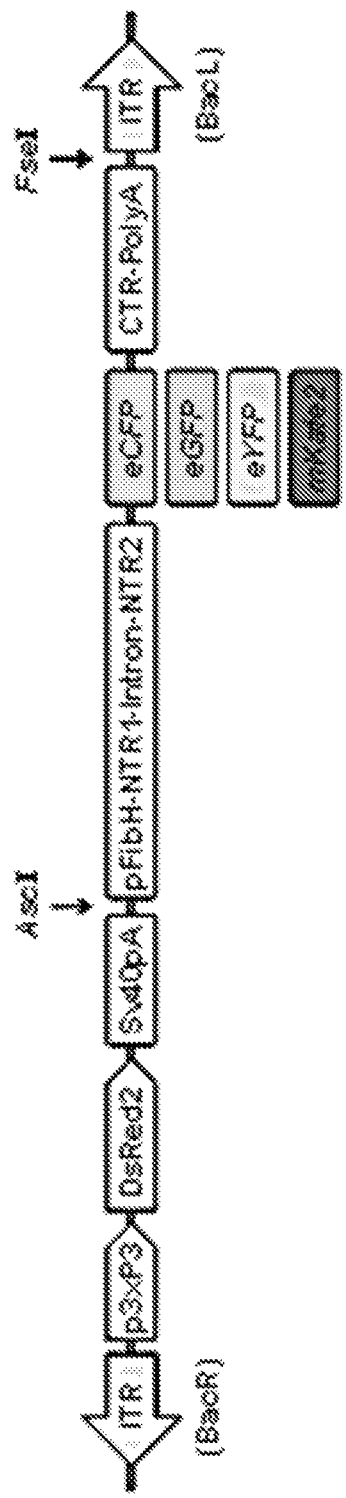
FIG. 2 is a transformation vector of p3xP3-DsRed2-FibH-(eCFP, eGFP, eYFP, or mKate2) for fluorescent silk production in silkworm transgenesis.

Specifically, we utilize fluorescent protein-expressed silk produced by transgenic silkworms as recombinant proteins via the piggyBac transposase method (see FIG. 2, discussed below). Silk proteins are an excellent biopolymer to be genetically hybridized with fluorescent protein genes. Second, to fabricate fluorescent silk microparticles (see FIG. 6, discussed below), fluorescent silk fibroin is regenerated into an aqueous solution with a low-temperature process, is freeze-dried, and is gently ground into zeolite-shaped microparticles with sizes of 99.3±7.9 μm (mean±standard deviation) (see FIGS. 1b and 1c and FIG. 7, discussed below). Third, an admixture of the fluorescent silk microparticles is broadcast on a large flat surface and a white silk fibroin solution is poured on top. After an ambient drying process in the dark, this thin transparent silk film with a thickness of 150 μm is punched into 7×7 $mm^2$ squares, resulting in all protein-based edible PUF devices (see FIGS. 6 and 8 discussed below). eCFP, eGFP, eYFP, and mKate2 silk cocoons possess bluish, greenish, yellowish, and reddish colors under white light illumination, respectively (see FIG. 3, discussed below). However, after the regeneration of the fluorescent silk, each type of fluorescent silk microparticles are not distinguishable with the naked eye, while maintaining their fluorescent properties (see FIGS. 1b-1e and FIG. 9, discussed below). This fabrication process is scalable for mass production without using any sophisticated equipment and is safe for oral consumption without any organic solvents or synthetic polymers (e.g. methanol, ethanol, isopropanol, or polyvinyl alcohol) (see FIG. 10, discussed below).

Figure 7:
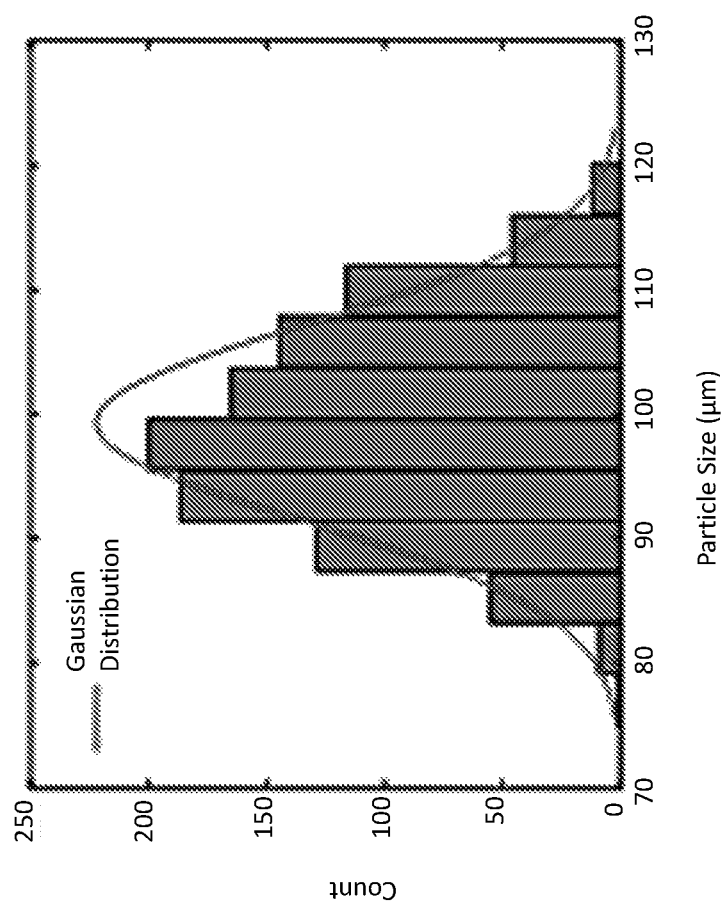
FIG. 7 is bar graph of size distribution of the fluorescent silk microparticles used in edible PUFs, according to the present disclosure

Referring to FIG. 1b, regenerated particulate eCFP, eGFP, eYFP and mKate2 silk produced by silkworm transgenesis via the piggyBac transposase method in which fluorescent proteins and silk (i.e. *Bombyx mori*) are genetically fused as recombinant proteins are shown. In FIG. 1b, the fluorescent images are acquired with the set of the excitation ($\lambda_{ex}$) and emission ($\lambda_{em}$) wavelengths, as specified on top of each photograph. The scale bar is 5 mm. FIG. 1c provides photograph of an edible PUF device in which fluorescent silk microparticles are embedded in a thin silk film. SEM image of fluorescent silk microparticles with zeolite-like shapes. FIG. 1d provides the emission spectra of particulate eCFP, eGFP, eYFP and mKate2 silk which cover a relatively broad wavelength range in the visible light, while the emission peak positions are not overlapped among others. FIG. 1e is confocal fluorescence microscopy images of the corresponding fluorescent silk microparticles under excitation of 405, 458, 514, or 561 nm. The scale bar is 100 µm. The size of fluorescent silk microparticles is 99.3±7.9 µm (mean±standard deviation), as shown in FIG. 7, as discussed below.

According to the present disclosure a cryptographic key is extracted from an output response when optically challenged, including the raw output measurement, the bitstream extraction, and the final digitized security key. According to one embodiment, four representative challenge-response pairs (n=4) are used based on the excitation and emission peak wavelengths of the individual fluorescent proteins in silk. An input challenge ($C_n$) is selected as a combination of the excitation and emission bands at specific wavelengths such as $\lambda_{ex}$=415 nm and $\lambda_{em}$=460 nm; $\lambda_{ex}$=470 and $\lambda_{em}$=510 nm; $\lambda_{ex}$=470 and $\lambda_{em}$=560 nm; $\lambda_{ex}$=530 and $\lambda_{em}$=630 nm, corresponding to eCFP, eGFP, eYFP, and mKate2 in silk, respectively. Upon optical excitation, a raw fluorescent image is recorded by a charge-coupled device (CCD) camera equipped with a conventional zoom lens via a tunable color filter that can be used for a down-stream optical recognition arrangement (see FIG. 11, discussed below).

Figure 3:
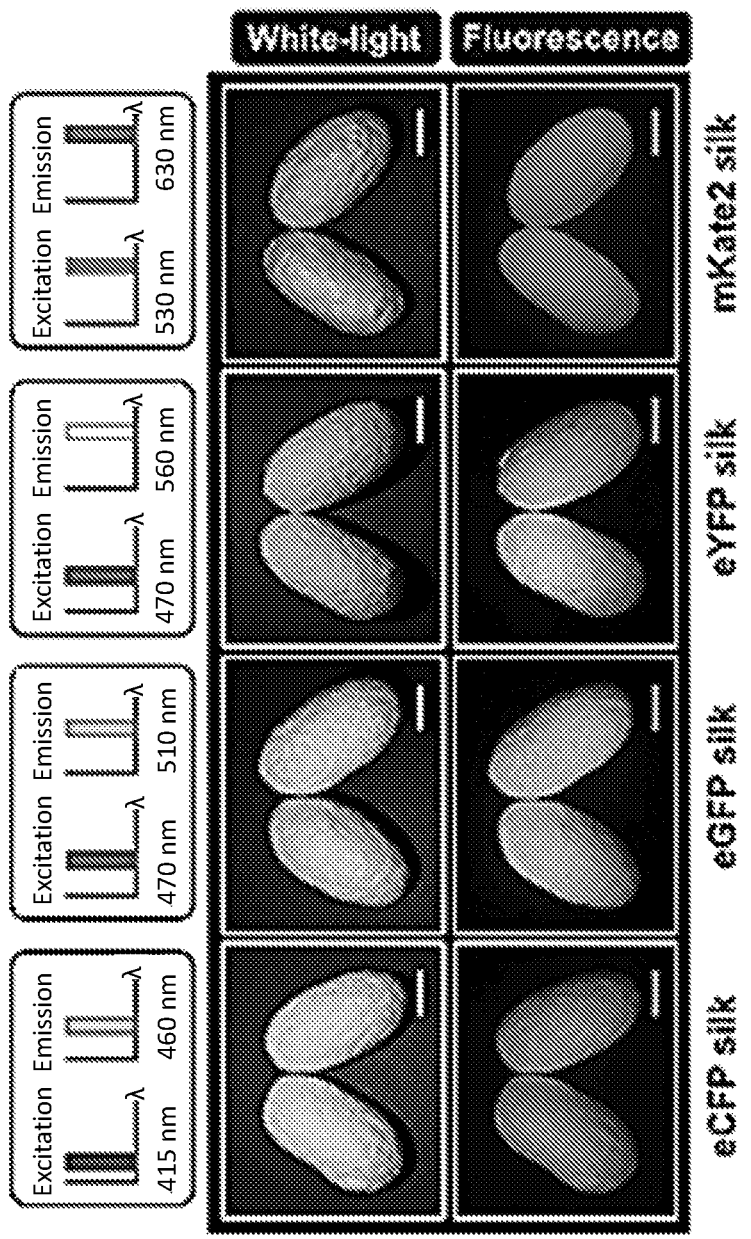
FIG. 3 provide white-light and fluorescent images of eCFP, eGFP, eYFP and mKate2 silk cocoons produced by silkworm transgenesis via the piggyBac transposase method.

Referring to FIG. 3, white-light and fluorescent images of eCFP, eGFP, eYFP and mKate2 silk cocoons produced by silkworm transgenesis via the piggyBac transposase method are shown. The fluorescent images are taken with the set of the excitation ($\lambda_{ex}$) and emission ($\lambda_{em}$) wavelengths, as specified on each photograph. The scale bar is 10 mm.

Figure 4:
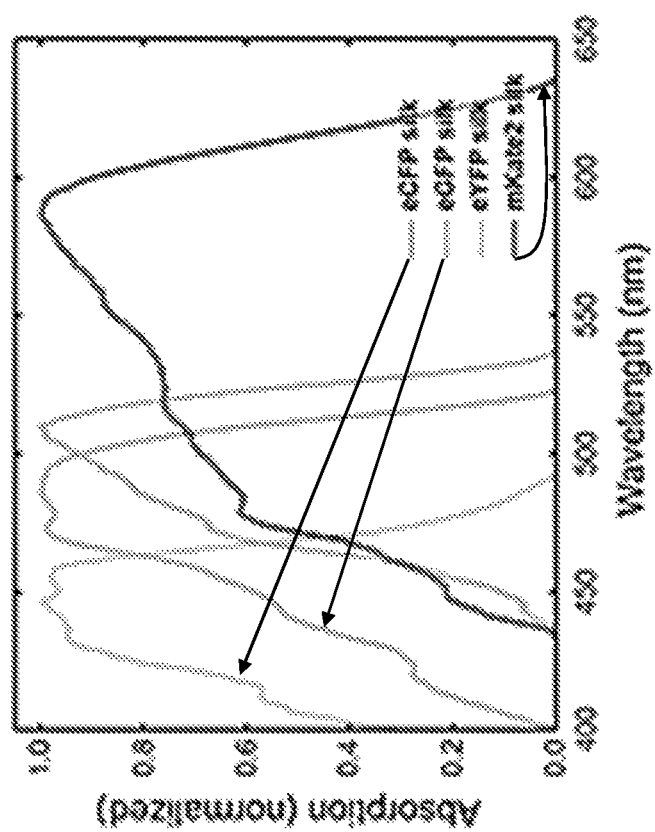
FIGS. 4 and 5 are graphs of normalized absorption and normalized intensity vs. wavelength in nm, respectively, for eCFP, eGFP, eYFP and mKate2.
Figure 5:
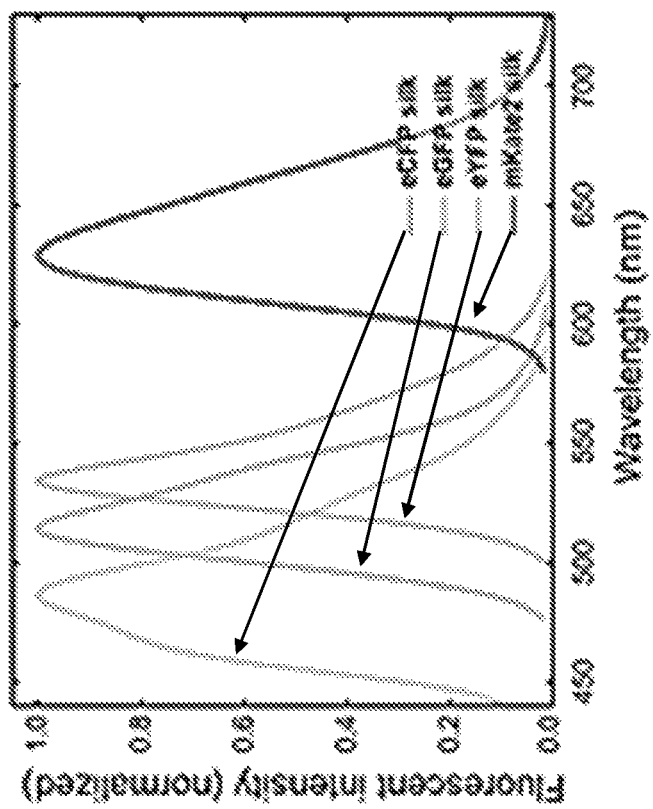

Referring to FIGS. 4 and 5, normalized absorption and fluorescence spectra of eCFP, eGFP, eYFP and mKate2 transgenic silk are shown. The excitation wavelengths are 415, 470, 470, and 530 nm for eCFP, eGFP, eYFP and mKate2 silk, respectively.

Figure 6:
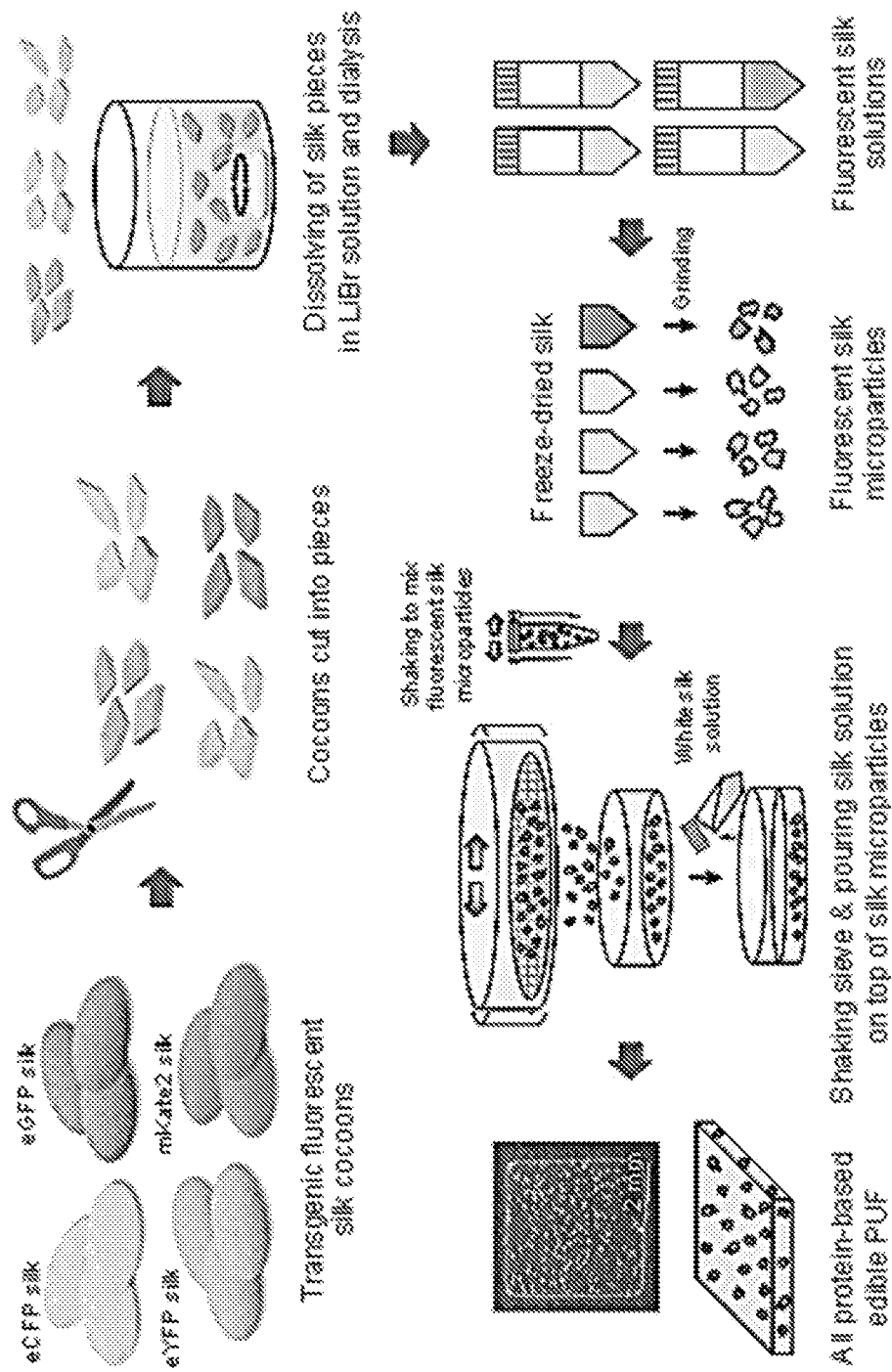
FIG. 6 is a schematic diagram of silk protein regeneration and edible PUF device fabrication using fluorescent silk (i.e. eCFP, eGFP, eYFP, and mKate2 silk) and natural white silk, according to the present disclosure.

Referring to FIG. 6, a schematic diagram of silk protein regeneration and edible PUF device fabrication using fluorescent silk (i.e. eCFP, eGFP, eYFP, and mKate2 silk) and natural white silk is shown, according to the present disclosure. Construction of plasmid vector DNA for silkworm transgenesis is first discussed. Using germline transformation (i.e. piggyBac transposon), the transition vectors pBac-3xP3-DsRed2-pFibH-(eCFP, eGFP, or eYFP) and pBac-3xP3-eGFP-pFibH-mKate2 were constructed as the piggyBac-derived vector and the injected the vector DNA with a helper vector into pre-blastoderm embryos. Referring to FIG. 2, a transformation vector of p3xP3-DsRed2-FibH-(eCFP, eGFP, eYFP, or mKate2) for fluorescent silk production in silkworm transgenesis is shown. In the case of mKate2, eGFP is used instead of DsRed2. The nucleotide sequences of pFibH-NTR and CTR are derived from Genebank Accession No. AF226688. pFibH: fibroin heavy chain promoter domain (1124 bp), NTR1: N-terminal region 1 (142 bp), intron: first intron (871 bp), NTR2: N-terminal region 2 (417 bp), CTR: C-terminal region (179 bp), PolyA: poly(A) signal region (301 bp), eCFP: enhanced cyan fluorescent protein, eGFP: enhanced green fluorescent protein, eYFP: enhanced yellow fluorescent protein, mKate2: monomeric far-red fluorescent protein, DsRed2: red fluorescent protein (a mutant form of DsRed from *Discosoma* sp.), ITR: inverted repeat sequences of piggyBac arms, 3xP3: 3xP3 promoter, and SV40: SV40 polyadenylation signal sequence. The restriction enzyme sites for the construction of recombinant vectors are indicated with the arrows For construction of plasmids, DsRed2 (eGFP for mKate2) cDNA as a marker was amplified by polymerase chain reaction (PCR) using specific primers with NheI/AflII sites from pDsRed2-C1 (NheI-DsRed2-F: 5'-GCTAG-CATGGCCTCCTCCGAGAAC-3' and DsRed2-AflII-R: 5'-CTTAAGCTACAGGAACAGGTGGTGGCG-3'; Clontech, Mountain View, CA, USA) and then cloned into the pGEM-T Easy Vector System (Promega, Co.), designated as pGEMT-DsRed2. DsRed2 gene was excised from pGEM-DsRed2 digested with restriction enzymes of NheI/AflII and replaced with eGFP gene from pBac-3xP3-eGFP to form pBac-3xP3-DsRed2. To obtain fibroin promoter, a DNA fragment containing the promoter domain (1,124 bp) and N-terminal region (1,430 bp) with the intron (972 bp) of the fibroin H gene (GenBank Accession No. AF226688, nt. 61,312-63,870) was amplified by PCR using the genomic DNA from *Bombyx mori* and primers (pFibHN-F: 5'-GGCGCGCCGTGCGTGATCAGGAAAAAT-3' and pFibHN-R: 5'-TGCACCGACTGCAGCACTAGTGCT-GAA-3'), subsequently cloned into pGEM-T Easy Vector System. The resultant DNA fragment was named as pGEMT-pFibH-NTR. The DNA fragment containing 180 bp of the 3' terminal sequence of the H-chain gen open reading frame (ORF) and 300 bp of the 3' region of the fibroin H gen (GenBank Accession No. AF226688, nt. 79,021-80,009) was amplified by PCR using genomic DNA from *Bombyx mori* and primers (pFibHC-F: 5'-AGCGTCAGTTACG-GAGCTGGCAGGGGA-3' and pFibHC-R: 5'-TATAGTAT-TCTTAGTTGAGAAGGCATA-3') and then was cloned into pGEM-T Easy Vector System. This fragment is designated as pGEMT-CTR. The fragments were prepared by digesting pGEMT-pFibH-NTR with AscI/SalI and pGEMT-CTR with SalI/SacI, respectively. These two fragments were cloned with pBluescriptII SK(−) vector (Stratagene) digested with ApaI/SalI, resulting in pFibHNC-null. Fluorescent genes (eCFP, eGFP, eYFP, and mKate2) were synthesized and purchased from the BIONEER corporation (South Korea). The N- and C-terminals had the NotI and SbfI restriction sites, respectively. The fluorescent genes were digested with NotI/SbfI and subcloned into a pFibHNC-null, resuling in pFibHNC-eCFP, pFibHNC-eGFP, pFibHNC-eYFP, and pFibHNC-mKate2, respectively. The resultant vector was named as pBac-3xP3-eCFP-FibH, pBac-3xP3-DsRed2-FibH-eGFP, pBac-3xP3-DsRed2-pFibH-eYFP, and pBac-3xP3-eGFP-FibH-mKate2, respectively.

To avoid heat-induced denaturation of fluorescent proteins in silk, we performed a dissolution process of fluorescent silk under a low temperature. Sericin of transgenic silk cocoons was removed with minimizing heat-induced denaturation of fluorescent proteins (i.e. eCFP, eGFP, eYFP, and mKate2). The silk cocoons were treated several times with a mixture solution of $Na_2CO_3$ (0.2%) at temperatures lower than 50° C., subsequently rinsed with warm deionized water (≈35° C.) several times. During a degumming process, the low pressure (620 mmHg) was additionally treated to completely remove the sericin. After degumming, the sericin-removed cocoons were dried under dark ambient conditions. For white silk, we used a conventional degumming method under a boiling process. It should be noted that $Na_2CO_3$ (also known as soda crystals) is an inactive ingredient for drug products approved by FDA. In addition, it is well known that natural silk also contains the elements of carbon (C), oxygen (O), and sodium (Na).

After sericin was removed, fluorescent silk cocoons were cut into small pieces with sizes less than 2-5 mm and then were dissolved in an aqueous solution of LiBr (9.5 M) at 45° C. for four hours with stirring of 400 rpm. The dissolved solution was filtered through a miracloth and was dialyzed in deionized water at room temperature for about two days with a cellulose semipermeable tube to remove the salt (i.e. LiBr). For eCFP, eGFP, eYFP, and mKate2 fluorescent silk, each regenerated silk fibroin solution with a concentration of about 5% (w v$^{-1}$) was obtained after centrifuging with a speed of 9000 rpm at about 4° C. for about 20 minutes. The regenerated solutions were freeze-dried at about −18° C. for seven days. The freeze-dried fluorescent silk was mechanically ground into granular microparticles with a mortar and pestle. Fluorescent silk microparticles with a size range of 90-106 μm were selected by shaking them through a stack of two standard test sieves with opening sizes of 90 and 106 μm. Similarly, a white silk fibroin solution was prepared in a dissolving solution of LiBr (9.5 M) at 60° C. for four hours with stirring of 400 rpm, resulting in a concentration of 4% (w v$^{-1}$). It was filtered through a miracloth and was dialyzed in deionized water at room temperature for about two days with a cellulose semipermeable tube, followed by centrifugation with a speed of 9000 rpm at about 4° C. for about 20 minutes.

To fabricate edible PUF devices, fluorescent silk microparticles were mixed at a ratio of 1:1:1:1 (eCFP, eGFP, eYFP, and mKate2 silk) in a microcentrifuge tube and then was shaken by hand. The admixture of the microparticles was broadcast to the surface of a polystyrene Petri dish (diameter 35 mm) through a sieve with an opening size of 106 μm by mechanical shaking. Subsequently, the natural white silk fibroin solution of 4 mL was poured on the plastic petri dish and was cast at ambient conditions (25±2° C. and 40-50% relative humidity) in the dark for three days, resulting in a silk film with a thickness of about 150 μm, including four different fluorescent silk microparticles. Edible PUFs were prepared by punching the silk films with a square area of 7×7 mm$^2$ (see FIG. 8, discussed below).

As easily accessible common light sources for optical excitation, we used ultraviolet, blue, and green light-emitting diodes (LEDs) with emission wavelengths of 415 nm (FWHM=14 nm), 470 nm (FWHM=25 nm), and 530 nm (FWHM=33 nm) purchased from Thorlabs Inc. (Newton, NJ, USA). Bandpass filters of 410, 470, and 530 nm (FB410-10, FB470-10, and FB530-10; Thorlabs Inc.) were placed between the light source and the PUF device. The optical power was kept at 1, 3, and 10 mW mm$^{-2}$ for 415-nm, 470-nm, and 530-nm LEDs at the surface of PUFs, respectively. To image the PUFs, we used a charge-coupled device (CCD) camera (Princeton Instruments PIXIS 1024B) with a conventional zoom lens (MVL7000, Navitar, Rochester, NY, USA) via a liquid crystal tunable filter with a FWHM of 7 nm (VariSpec VIS-07-20; PerkinElmer, Inc., Waltham, MA, USA). As a result, the following set of excitation and emission bands was selected such that $\lambda_{ex}$=415 nm and $\lambda_{em}$=460 nm; $\lambda_{ex}$=470 and $\lambda_{em}$=510 nm; $\lambda_{ex}$=470 and $\lambda_{em}$=560 nm; $\lambda_{ex}$=530 and $\lambda_{em}$=630 nm, optimized for eCFP, eGFP, eYFP, and mKate silk, respectively.

According to one embodiment of the present disclosure, during the regeneration process for the fabrication of colored silk particles, edible fluorescent color dyes (Table 2) can be mixed with a dissolved silk protein solution or an edible polymer solution. Specifically, edible fluorescent color dyes can be used as a color source for the realization of colored silk particles in addition to transgenic fluorescent silk. The color dyes can be easily dissolved in water and integrated with silk proteins or polymers during the regeneration process.

Figure 8:
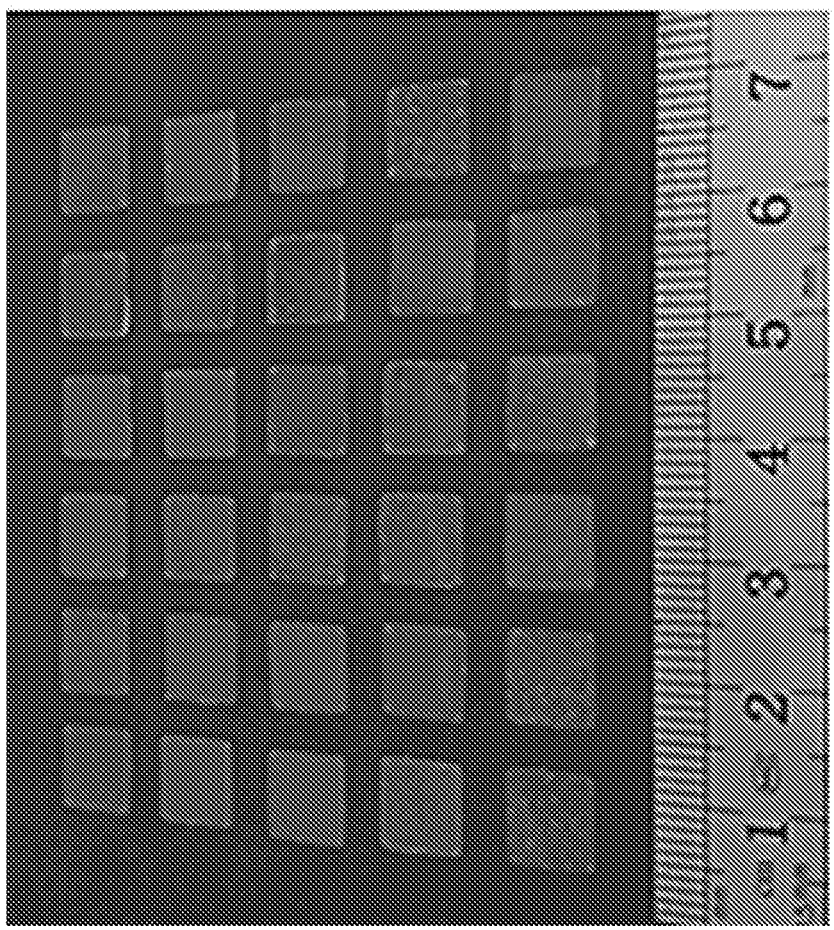
FIG. 8 is a photograph of 30 different edible PUF devices used to characterize the overall PUF performance, according to the present disclosure.
Figure 9:
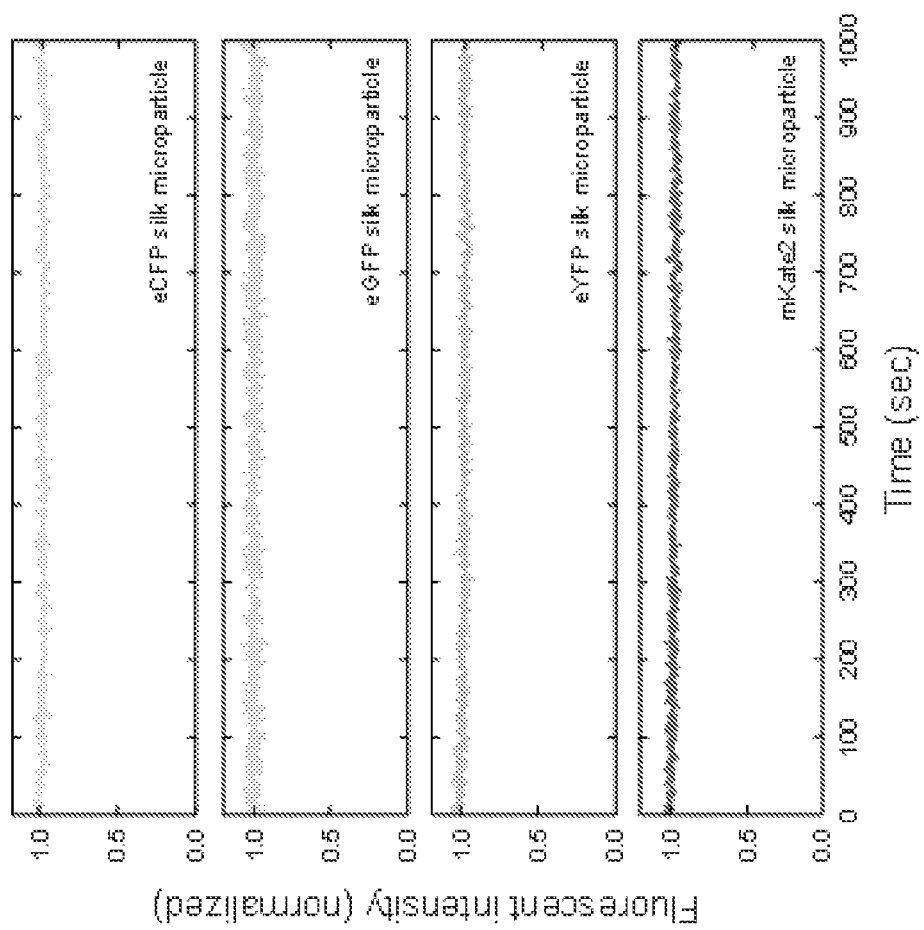
FIG. 9 is a series of fluorescent intensity vs. time (sec) are shown depicting temporal photostability of eCFP, eGFP, eYFP, and mKate2 silk microparticles under excitation of 440 nm for eCFP, eGFP, and eYFP silk; 514 nm for mKate2 silk.
Figures 10A, 10B:
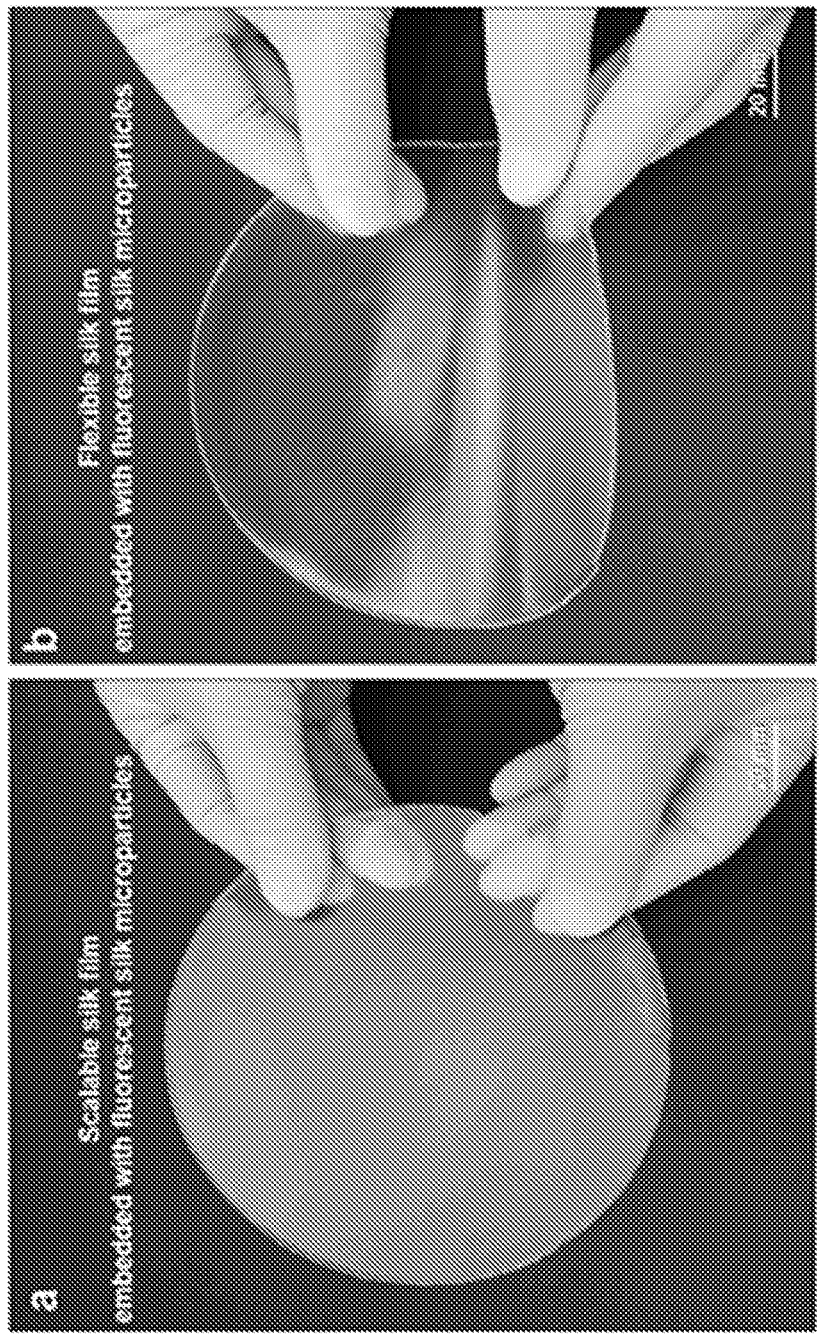
FIGS. 10a and 10b are two photographs depicting scalability (FIG. 10a) and flexibility (FIG. 10b) of the proposed edible PUFs for mass production and easy integration with medicines.

Referring to FIG. 7, a bar graph of size distribution of the fluorescent silk microparticles used in edible PUFs is shown, according to the present disclosure. The particle sizes are characterized from SEM images. A Gaussian fit returns a mean of 99.3 μm and a standard deviation (SD) of 7.9 μm. Referring to FIG. 8, a photograph of 30 different edible PUF devices used to characterize the overall PUF performance is provided, according to the present disclosure. Each size is 7×7 mm$^2$. Referring to FIG. 9, a series of fluorescent intensity vs. time (sec) are shown depicting temporal photostability of eCFP, eGFP, eYFP, and mKate2 silk microparticles under excitation of 440 nm for eCFP, eGFP, and eYFP silk; 514 nm for mKate2 silk. The emission intensity is measured through a 458-nm lowpass filter for eCFP, eGFP, and eYFP silk; a 550-nm lowpass filter for mKate2 silk over 1000 seconds. Referring to FIGS. 10a and 10b, two photographs are shown depicting scalability (FIG. 10a) and flexibility (FIG. 10b) of the proposed edible PUFs for mass production and easy integration with medicines.

Figure 11:
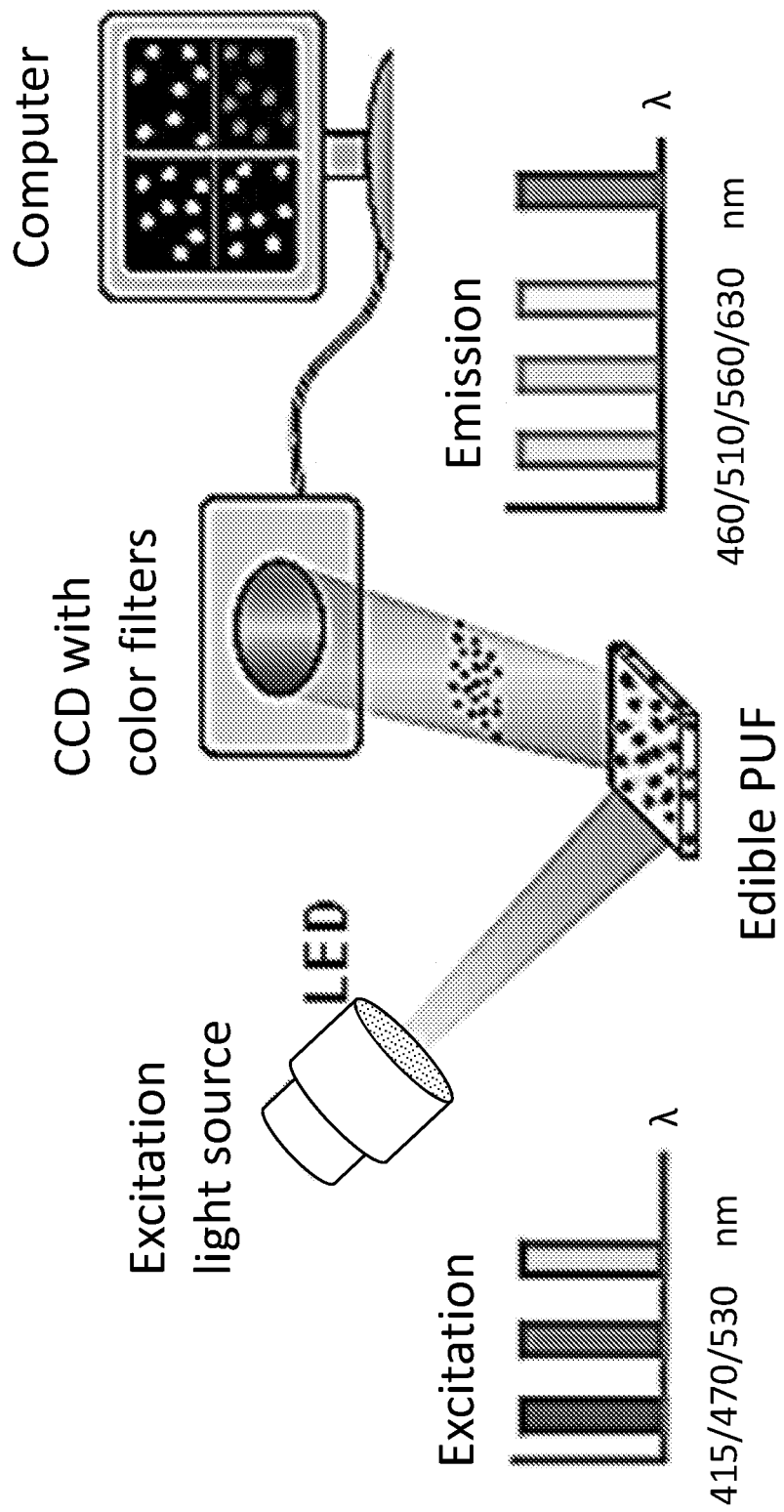
FIG. 11 is a schematic diagram of an exemplary customized imaging setup according to the present disclosure for obtaining fluorescent images of edible PUF devices.

Referring to FIG. 11, a schematic diagram of an exemplary customized imaging setup according to the present disclosure is provided for obtaining fluorescent images of edible PUF devices. As easily accessible common light sources for optical excitation, ultraviolet, blue, and green light-emitting diodes (LEDs) at central wavelengths of 415, 470, and 530 nm are used. Fluorescent images are acquired through a liquid crystal tunable filter with emission wavelengths of 460, 510, 560, and 630 nm with acquisition times of 60, 5, 40, and 30 sec, respectively. Different combination sets of the excitation and emission wavelengths serve as challenges to realize the parametric support of challenge-response pairs in edible PUFs. Given some high-end smartphones already have multiple light sources (e.g. flashlight LED), we envision that multiple different colored LEDs can easily be embedded into a smartphone as manufacturers realize a variety of direct applications, including the proposed on-dose authentication.

Figure 12:
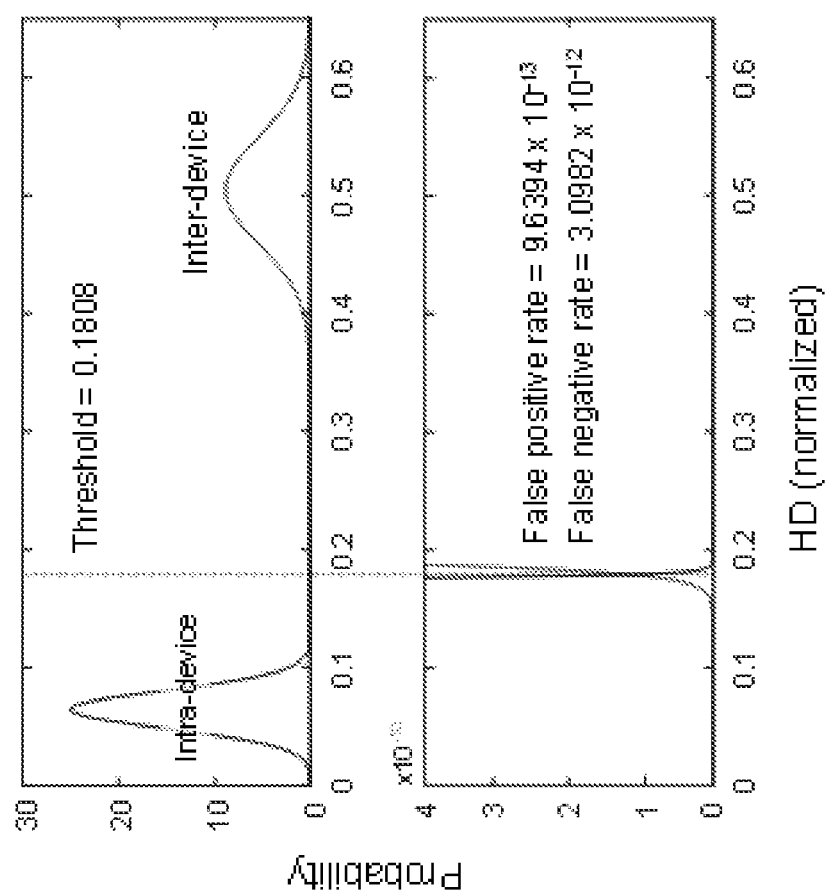
FIG. 12 provides graphs of probability vs. normalized hamming distance (HD) to show intra-device (reproducibility) and inter-device (uniqueness) variabilities with a cut-off threshold of 0.1808.
Figure 13:
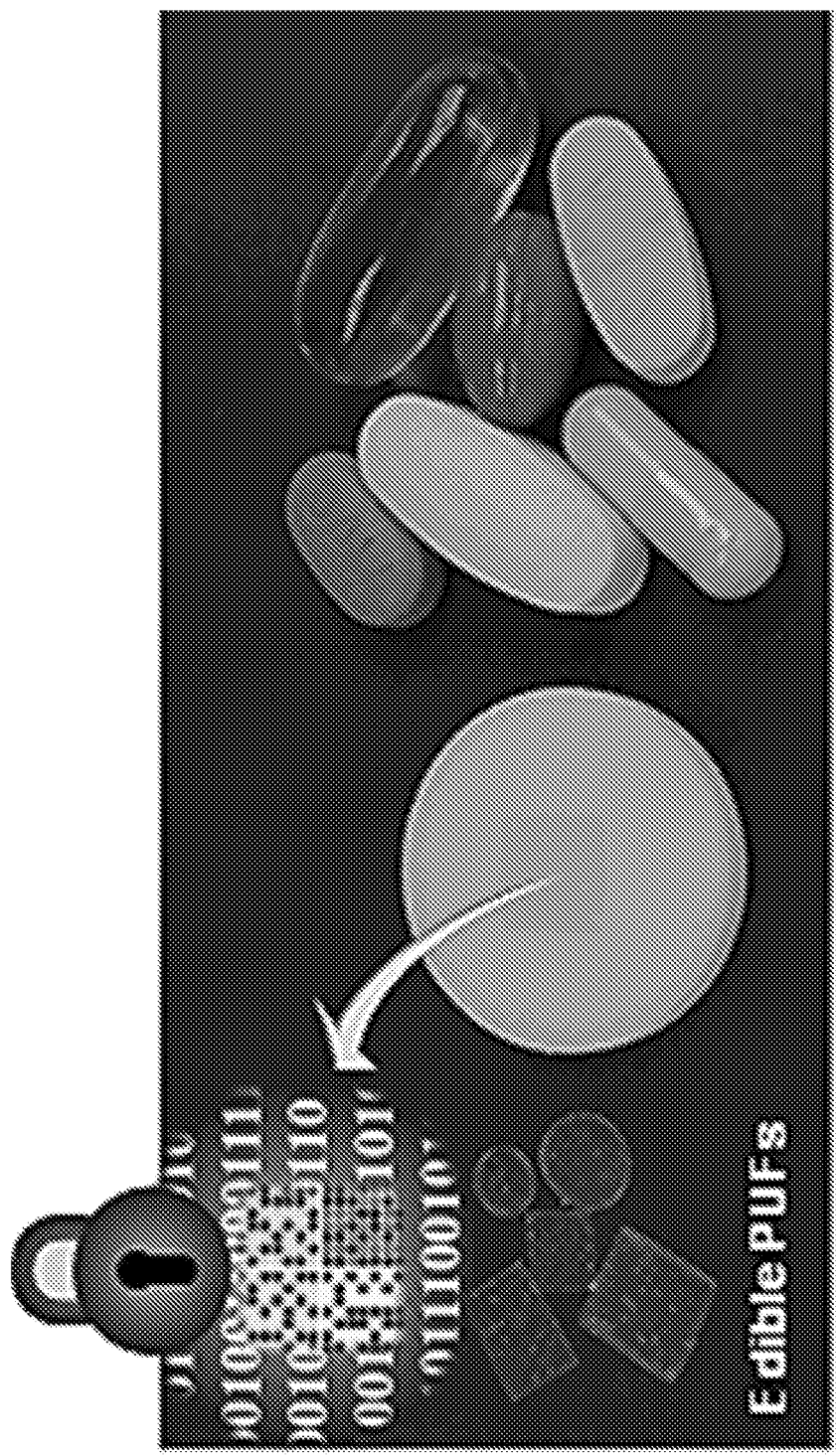
FIG. 13 is a schematic showing feasibility of on-dose (or in-dose) authentication using edible PUFs.
Figure 14:
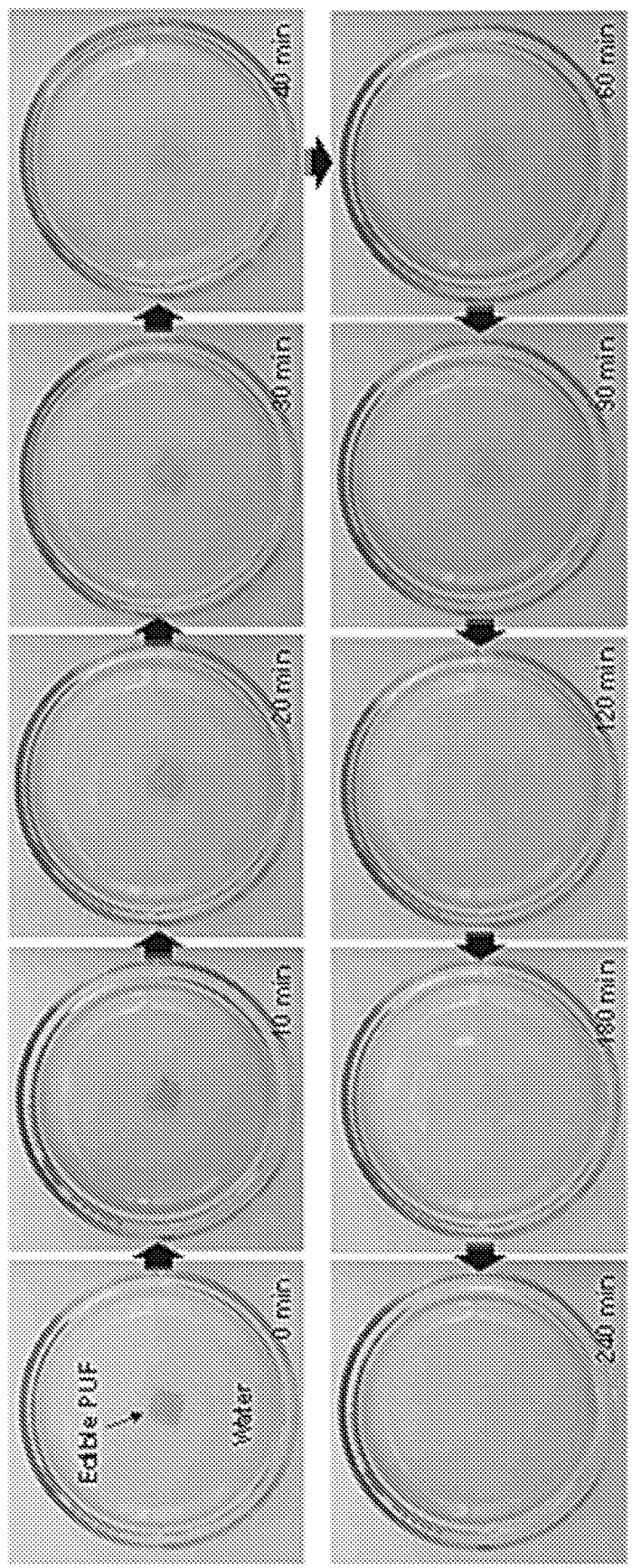
FIG. 14 provides a series of photographs to depict the water solubility of edible PUFs composed of silk proteins and fluorescent proteins, according to the present disclosure.

Referring to FIG. 12, graphs of probability vs. normalized hamming distance (HD) are provided to show intra-device (reproducibility) and inter-device (uniqueness) variabilities with a cut-off threshold of 0.1808. The resulting false positive and false negative rates are 9.6394×10$^{-13}$ and 3.0982×10$^{-12}$, respectively. Referring to FIG. 13, a complex photograph of pharmaceuticals is shown to depict feasibility of on-dose (or in-dose) authentication using edible PUFs, according to the present disclosure. Referring to FIG. 14, a series of photographs is shown to depict the water solubility of edible PUFs composed of silk proteins and fluorescent proteins, according to the present disclosure. The natural silk fibroin film embedded with eCFP, eGFP, eYFP, and mKate2 silk microparticles (loaded with methylene blue for easy visualization purpose) in deionized water is completely dissolved in 240 minutes at room temperature.

Figure 15:
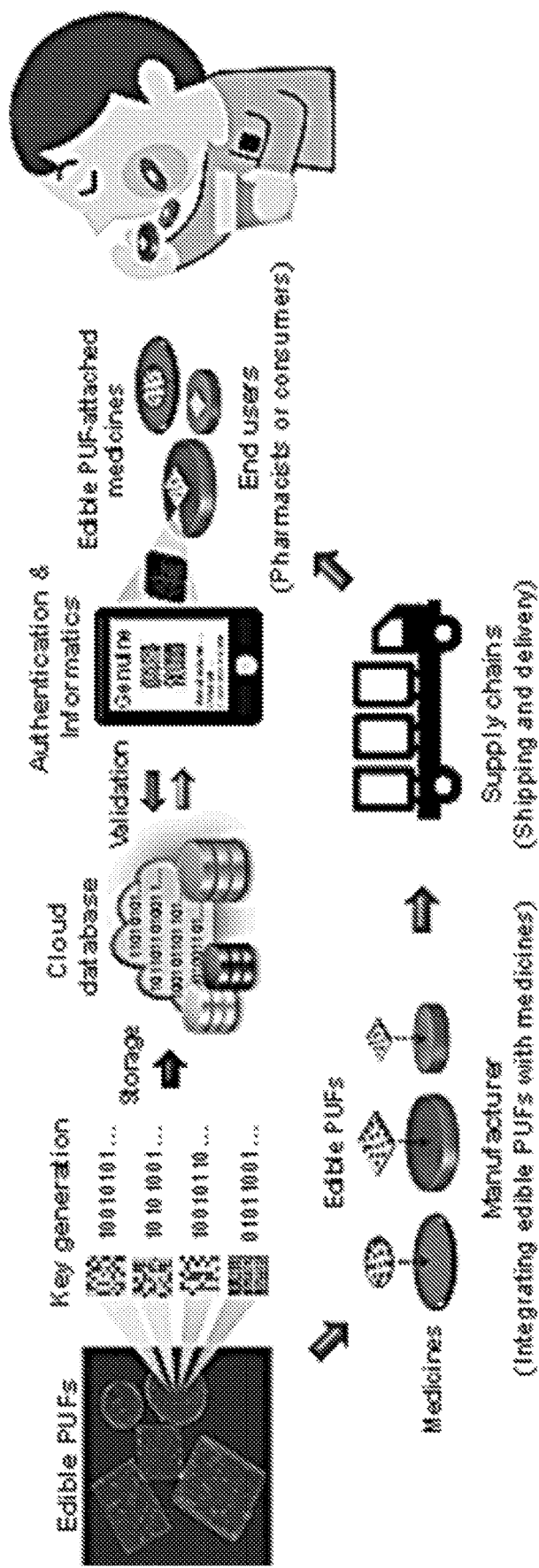
FIG. 15 is a schematic of a concept of on-dose authentication, where each individual medicine in a solid oral dosage form (e.g. tablets and capsules) is integrated with an edible PUF device by the pharmaceutical manufacturer.

One prominent application of the reported edible PUFs is on-dose authentication to prevent patients from taking counterfeit pharmaceutical products. Referring to FIG. 15, an exemplary schematic of the process flow representing such authentication is shown. The edible PUF, which is flexible (see FIG. 10b), can be attached to the surface of medicines in a solid oral dosage form including pills, tablets, and capsules. Each medicine possesses unique challenge-response pairs and the end user can verify genuine or fake using a smartphone camera or a customized reader and accessing the registered digital keys in a database (e.g. cloud) where each validation is guided with a trusted authority against the digital identity. Indeed, the edible PUF has a self-vanishing feature. Silk proteins (i.e. fibroin) are easily be dissolved in an aqueous solution without any special treatments, owing to the disintegration property and proteolytic activity (i.e. enzymatic degradation). When the reported edible PUF is loaded with a blue dye (i.e. methylene blue) for easy visual detection purpose, it is completely dissolved in deionized water after 240 minutes (see FIG. 14), also supporting the use for oral consumption. In other words, the end user (i.e. patient) can take the medicine without removing the PUF from the surface.

It should be appreciated that in addition to the material discussed herein, other materials including edible polymers, edible proteins, and edible dyes can be used for the PUF. For example, one or more of the following edible polymers can be used in the PUF of the present disclosure: the edible polymers are selected from the group consisting of Starch, cellulose derivatives, chitosan, pectin, alginates, gums, carrageenans, and combinations thereof. In addition, one or more of the following edible polymers can be used in the PUF of the present disclosure: gelatin, collagen, albumin, milk protein, and combinations thereof. In addition, one or more of the following edible polymers can be used in the PUF of the present disclosure: zein, soy, wheat gluten, lectins, and combinations thereof. In addition, one or more of the following edible polymers can be used in the PUF of the present disclosure: Fatty acids, triglycerides, phospholipids, and combinations thereof. In addition, one or more of the following edible fluorescent proteins can be used in the PUF of the present disclosure: red fluorescent protein (DsRed), orange fluorescent protein (mKO), and a combination thereof. In addition, one or more of the following edible fluorescent dyes can be used in the PUF of the present disclosure: Brilliant Blue FCF, Indigotine, Fast Green FCF, Erythrosine, Allura Red AC, Tartrazine, Sunset Yellow FCF, and combinations thereof, as provided in Table 2, below.

can be obtained from these particles and a cryptographic key generated representing an original authentication pattern. This cryptographic key is then stored in a secured database awaiting authentication by an end user. The image can be obtained at the source of the pharmaceutical by a single image capture device representing an X-Y cryptographic key (i.e., a two-dimensional image) or by more than one image capture device (e.g., stereo-photography) representing an X-Y-Z cryptographic key (i.e., a three-dimensional image for a pharmaceutical with curvatures in the Z-direction).

According to another embodiment, the anti-counterfeit measures can directly be incorporated using spray deposition as an additive manufacturing process, resulting in security key-embedded pharmaceutical products. To support the unclonability (i.e. asymmetricity), it is critical to include a source of entropy (physical disorder) in a scalable manner. In other words, a spray system serves as a scalable entropy source for randomness. Such spray deposition of silk microparticles have unpredictable variations due to the stochastic nature of atomization as well as the impingement dynamics. Even with the same spraying process, it is virtually impossible to duplicate or clone the previously generated patterns. Thus, this manufacturing approach makes the PUF printing more cost-effective and scalable.

Towards this end, solid silk microparticles are deposited with a low density on the surface of medicines in a scalable manner with a commercially available cold spray system. In cold spraying, solid microparticles (powders) are accelerated in a supersonic gas jet. During impact with the substrate, microparticles undergo plastic deformation and adhere to the surface. Silk microparticles are fed from the divergent section of the nozzle and are accelerated by a driving gas to the target surface. In doing so, the microparticles are impregnated onto the surface of the pharmaceutical

TABLE 2

Food dye colorings approved by the U.S. Food and Drug Administration. FD&C stands for laws passed by the U.S. Congress in 1938, called the Federal Food, Drug, and Cosmetic Act.

| FD&C Designation | Name | Color | Excitation/ Emission wavelengths [1] | Molecular Formula |
|---|---|---|---|---|
| Blue No. 1 | Brilliant Blue FCF | Blue | 580-600 nm/ 650-700 nm | $C_{37}H_{34}N_2Na_2O_9S_3$ |
| Blue No. 2 | Indigotine | Indigo | — | $C_{16}H_8N_2Na_2O_8S_2$ |
| Green No. 3 | Fast Green FCF | Turquoise | 580-600 nm/ 650-700 nm | $C_{37}H_{34}N_2Na_2O_{10}S_3$ |
| Red No. 3 | Erythrosine | Pink | — | $C_{20}H_6I_4Na_2O_5$ |
| Red No. 40 | Allura Red AC | Red | 450-540 nm/ 540-610 nm | $C_{18}H_{14}N_2Na_2O_8S_2$ |
| Yellow No. 5 | Tartrazine | Yellow | 450-540 nm/ 540-610 nm | $C_{16}H_9N_4Na_3O_9S_2$ |
| Yellow No. 6 | Sunset Yellow FCF | Orange | 450-540 nm/ 540-610 nm | $C_{16}H_{10}N_2Na_2O_7S_2$ |

It should be appreciated that according to the present disclosure, particles are applied either i) to a substrate or ii) to a pharmaceutical directly. The substrate can be made of an edible silk or an edible polymer, according to the present disclosure. The particles can be one or more of edible silk (e.g., edible fluorescent silk), edible dyes (e.g., edible fluorescent dyes), edible polymers, according to the present disclosure. These particles can be cast into a random pattern onto either the substrate, or the pharmaceutical directly. Alternatively, these particles can be sprayed onto either the substrate, or the pharmaceutical directly in order to generate a random pattern. Once the particles are applied, an image and thus fixed in place. Once fixed, these microparticles can be challenged by light to generate a response in the form of a cryptographic key that can be recorded in a remote database for later confirmation. This confirmation is based on application of light at different wavelengths at later time, which will generate a cryptographic pattern that can be checked against the cryptographic key.

Those having ordinary skill in the art will recognize that numerous modifications can be made to the specific implementations described above. The implementations should not be limited to the particular limitations described. Other implementations may be possible.

The invention claimed is:

1. A method of generating a physically unclonable function for pharmaceutical authentication, comprising:
    generating an edible physically unclonable function (PUF);
    affixing the edible PUF onto a pharmaceutical in a random distribution; and
    generating a cryptographic key based on the randomly distributed and affixed edible PUF,
    wherein the edible PUF is based on randomly distributed fluorescent protein-expressed silk particles,
    wherein the fluorescent protein-expressed silk can be produced by transgenesis of genetically engineered domesticated silkworms.

2. The method of claim 1, wherein the edible PUF comprises edible polymers.

3. The method of claim 2, the edible polymers are selected from the group consisting of Starch, cellulose derivatives, chitosan, pectin, alginates, gums, carrageenans, and combinations thereof.

4. The method of claim 2, the edible polymers are selected from the group consisting of gelatin, collagen, albumin, milk protein, and combinations thereof.

5. The method of claim 2, the edible polymers are selected from the group consisting of zein, soy, wheat gluten, lectins, and combinations thereof.

6. The method of claim 2, the edible polymers are selected from the group consisting of Fatty acids, triglycerides, phospholipids, and combinations thereof.

7. The method of claim 1, wherein the transgenes is expressed by germline transformation using gene splicing.

8. The method of claim 7, wherein the gene splicing is based on piggyBac.

9. The method of claim 1, wherein the fluorescent silk protein is selected from the group consisting of enhanced cyan fluorescent protein (eCFP), enhanced green fluorescent protein (eGFP), enhanced yellow fluorescent protein (eYFP), and mKate2 (far-red) fluorescent protein.

10. A method of generating a physically unclonable function for pharmaceutical authentication, comprising:
    generating an edible physically unclonable function (PUF);
    affixing the edible PUF onto a pharmaceutical in a random distribution; and
    generating a cryptographic key based on the randomly distributed and affixed edible PUF,
    wherein the edible PUF is based on randomly distributed fluorescent protein-expressed silk particles, and
    wherein the fluorescent silk protein is selected from the group consisting of enhanced cyan fluorescent protein (eCFP), enhanced green fluorescent protein (eGFP), enhanced yellow fluorescent protein (eYFP), and mKate2 (far-red) fluorescent protein.

11. The method of claim 10, wherein the edible PUF comprises edible polymers.

12. The method of claim 11, the edible polymers are selected from the group consisting of Starch, cellulose derivatives, chitosan, pectin, alginates, gums, carrageenans, and combinations thereof.

13. The method of claim 11, the edible polymers are selected from the group consisting of gelatin, collagen, albumin, milk protein, and combinations thereof.

14. The method of claim 11, the edible polymers are selected from the group consisting of zein, soy, wheat gluten, lectins, and combinations thereof.

15. The method of claim 11, the edible polymers are selected from the group consisting of Fatty acids, triglycerides, phospholipids, and combinations thereof.

16. The method of claim 10, wherein the fluorescent protein-expressed silk can be produced by transgenesis of genetically engineered domesticated silkworms.

17. The method of claim 16, wherein the transgenes is expressed by germline transformation using gene splicing.

18. The method of claim 17, wherein the gene splicing is based on piggyBac.

19. A method of generating a physically unclonable function for pharmaceutical authentication, comprising:
    generating an edible physically unclonable function (PUF);
    affixing the edible PUF onto a pharmaceutical in a random distribution; and
    generating a cryptographic key based on the randomly distributed and affixed edible PUF,
    wherein the edible PUF comprises edible polymers,
    wherein the edible polymers are selected from (i) from the group consisting of Starch, cellulose derivatives, chitosan, pectin, alginates, gums, carrageenans, and combinations thereof, (ii) from the group consisting of gelatin, collagen, albumin, milk protein, and combinations thereof, (iii) from the group consisting of zein, soy, wheat gluten, lectins, and combinations thereof, or (iv) from the group consisting of Fatty acids, triglycerides, phospholipids, and combinations thereof.

20. The method of claim 19, wherein the edible PUF is based on randomly distributed fluorescent protein-expressed silk particles.

21. The method of claim 20, wherein the fluorescent protein-expressed silk can be produced by transgenesis of genetically engineered domesticated silkworms.

22. The method of claim 21, wherein the transgenes is expressed by germline transformation using gene splicing.

23. The method of claim 22, wherein the gene splicing is based on piggyBac.

24. The method of claim 19, wherein the fluorescent silk protein is selected from the group consisting of enhanced cyan fluorescent protein (cCFP), enhanced green fluorescent protein (eGFP), enhanced yellow fluorescent protein (eYFP), and mKate2 (far-red) fluorescent protein.

* * * * *